(12) United States Patent
Hamiche

(10) Patent No.: US 9,150,628 B2
(45) Date of Patent: Oct. 6, 2015

(54) PARP INHIBITORS

(75) Inventor: Ali Hamiche, Villejuif (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 1390 days.

(21) Appl. No.: 12/084,873

(22) PCT Filed: Nov. 14, 2006

(86) PCT No.: PCT/IB2006/003224
§ 371 (c)(1),
(2), (4) Date: Dec. 29, 2008

(87) PCT Pub. No.: WO2007/054814
PCT Pub. Date: May 18, 2007

(65) Prior Publication Data
US 2010/0323974 A1 Dec. 23, 2010

Related U.S. Application Data

(60) Provisional application No. 60/736,588, filed on Nov. 14, 2005.

(51) Int. Cl.
*A61K 38/00* (2006.01)
*C07K 14/47* (2006.01)

(52) U.S. Cl.
CPC *C07K 14/47* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,032,617 A | 7/1991 | Lee et al. | |
| 5,041,653 A | 8/1991 | Lee et al. | |
| 5,177,075 A | 1/1993 | Suto et al. | |
| 5,215,738 A | 6/1993 | Lee et al. | |
| 5,589,483 A | 12/1996 | West | |
| 5,730,969 A | 3/1998 | Hora et al. | |
| 5,756,510 A | 5/1998 | Griffin et al. | |
| 5,981,221 A * | 11/1999 | Hillman et al. | 435/69.1 |
| 6,136,314 A * | 10/2000 | Hillman et al. | 424/192.1 |
| 6,638,502 B1 | 10/2003 | Li et al. | |
| 7,842,467 B1 * | 11/2010 | Heidbrink et al. | 435/7.1 |
| 2004/0265273 A1 | 12/2004 | Li et al. | |
| 2007/0054401 A1 | 3/2007 | Prochiantz et al. | |
| 2007/0105181 A1 * | 5/2007 | Pope et al. | 435/23 |
| 2007/0280879 A1 * | 12/2007 | Glassy et al. | 424/1.11 |

FOREIGN PATENT DOCUMENTS

| | | |
|---|---|---|
| EP | 0 386 882 | 9/1990 |
| EP | 1 512 696 | 3/2005 |
| EP | 1 526 183 | 4/2005 |
| JP | 2005052101 A | 3/2005 |
| WO | WO 97/04771 | 2/1997 |
| WO | WO 97/12622 | 4/1997 |
| WO | WO 98/33802 | 8/1998 |
| WO | WO 99/11622 | 3/1999 |
| WO | WO 99/11623 | 3/1999 |
| WO | WO 99/11624 | 3/1999 |
| WO | WO 99/11628 | 3/1999 |
| WO | WO 99/11644 | 3/1999 |
| WO | WO 99/11645 | 3/1999 |
| WO | WO 99/11649 | 3/1999 |
| WO | WO 01/27300 | 4/2001 |
| WO | WO 02/10201 | 2/2002 |
| WO | WO 2004/069279 | 8/2004 |

OTHER PUBLICATIONS

Chakravarthy et al. (Molec.& Cell. Biol., vol. 25, No. 17, pp. 7616-7624).*
Nusinow (JBC, vol. 282, No. 17, pp. 12851-12859).*
International Search Report for PCT/IB2006/003224, dated Apr. 3, 2007, 4 pages.
Angelov, Dimitar et al.; "The Histone Variant MacroH2A Interferes with Transcription Factor Binding and SWI/SNF Nucleosome Remodeling;" Molecular Cell, vol. 11, No. 4, XP-002425980; Apr. 1, 2003; pp. 1033-1041.
Perche, Pierre-Yves et al.; "Higher Concentrations of Histone MacroH2A in the Barr Body are Correlated with Higher Nucleosome Density;" Current Biology, vol. 10, No. 23, XP-002425981, Nov. 30, 2000; pp. 1531-1534.
Allen, Mark D. et al.; "The Crystal Structure of AP1521 a Protein From *Archaeoglobus fulgidus* with Homology to the Non-Histone Domain of MacroH2A;" Journal of Molecular Biology, London, GB, vol. 330, No. 3, Jul. 11, 2003; pp. 503-511.
Karras, Georgios I et al.; "The *Macro* Domain is an ADP-Ribose Binding Module;" The EMBO Journal, vol. 24, No. 11, XP-002425982, Jun. 1, 2005; pp. 1911-1920.

(Continued)

*Primary Examiner* — Hope Robinson
(74) *Attorney, Agent, or Firm* — Harness, Dickey & Pierce, P.L.C.

(57) ABSTRACT

The present invention relates to new inhibitors of the nucleic enzyme poly(adenosine 5'-diphospho-ribose) polymerase ["poly(ADP-ribose) polymerase" or "PARP", which is also sometimes called "PARS" for poly(ADP-ribose) synthetase]. More particularly, the invention relates to the use of PARP inhibitors to prevent and/or treat tissue damage resulting from cell damage or death due to necrosis or apoptosis; neural tissue damage resulting from ischemia and reperfusion injury; neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells.

13 Claims, 24 Drawing Sheets

(56) References Cited

OTHER PUBLICATIONS

Aguiar, Ricardo C.T. et al.; "B-Aggressive Lymphoma Family Proteins Have Unique Domains That Modulate Transcription and Exhibit Poly(ADP-Ribose) Polymerase Activity;" The Journal of Biological Chemistry; vol. 280, No. 40, XP-002425983, Oct. 7, 2005; pp. 33756-33765.

Kustatscher, Georg et al.; "Splicing Regulates NAD Metabolite Binding to Histone MacroH2A;" Nature Structural & Molecular Biology; vol. 12, No. 7, XP-002425984, Jul. 2005; pp. 624-625.

Chakravarthy, Srinivas et al.; "Structural Characterization of the Histone Variant MacroH2A;" Molecular and Cellular Biology, vol. 25, No. 17, XP-002426137, Sep. 2005; pp. 7616-7624.

Chadwick, Brian P. et al.; "Histone Variant MacroH2A Contains Two Distinct Macrochromatin Domains Capable of Directing MacroH2A to the Inactive X Chromosome;" Nucleic Acids Research, vol. 29, No. 13, XP-002425985, Jul. 1, 2001; pp. 2699-2705.

Ouararhni, Khalid et al.; "The Histone Variant mH2A1.1 Interferes With Transcription by Down-Regulating PARP-1 Enzymatic Activity;" Genes & Development, vol. 20, No. 23, XP008076718, Dec. 1, 2006; pp. 3324-3336.

Zhang, J. et al.; "Nitric Oxide Activation of Poly(ADP-Ribose) Synthetase in Neurotoxicity;" Science, vol. 263, Feb. 4, 1994; pp. 687-689.

Wallis, R. A. et al.; "Neuroprotection Against Nitric Oxide Injury With Inhibitors of ADP-Ribosylation;" NeuroReport, vol. 5, No. 3, Dec. 13, 1993; pp. 245-248.

Endres, M. et al.; "Ischemic Brain Injury Is Mediated by the Activation of Poly(ADP-Ribose) Polymerase;" Journal of Cerebral Blood Flow & Metabolism, vol. 17, No. 11, 1997; pp. 1143-1151.

Wallis, R. A. et al.; "Traumatic Neuroprotection With Inhibitors of Nitric Oxide and ADP-Ribosylation;" Brain Research, vol. 710, 1996; pp. 169-177.

Thiemermann, C. et al.; "Inhibition of the Activity of Poly(ADP Ribose) Synthetase Reduces Ischemia-Reperfusion Injury in the Heart and Skeletal Muscle;" Proc. Natl. Acad. Sci. USA, vol. 94, Jan. 1997; pp. 679-683.

Wolff, M. E.; "Emerging Drugs: The Prospect for Improved Medicines;" Ashley Publications, Ltd., London, 1999, Book Review in Jounal of Medicinal Chemistry, vol. 42, No. 15; 1999; 2 pages.

Zhang, J. et al.; "Poly(ADP-Ribose) Synthetase Activation: An Early Indicator of Neurotoxid DNA Damage;" J. Neurochem., vol. 65, No. 3, 1995; pp. 1411-1414.

Cosi, C. et al.; "Poly(ADP-Ribose) Polymerase (PARP) Revisited;" Ann. N.Y. Acad. Sci., vol. 825, 1997; pp. 366-379.

Cosi, C. et al.; "Poly(ADP-Ribose) Polymerase Inhibitors Protect Against MPTP-Induced Depletions of Striatal Dopamine and Cortical Noradrenaline in C57BI/6 Mice;" Brain Research, vol. 729, 1996; pp. 264-269.

Dawson T. M., et al.; "Protection of the Brain From Ischemia;" Excerpt from Chapter 25 of Cerebrovascular Disease, H. Hunt Batjer ed., 1997; pp. 319-325.

Dawson, V. L. et al.; "Nitric Oxide Mediates Glutamate Neurotoxicity in Primary Cortical Cultures;" Proc. Natl. Acad. Sci. USA, vol. 88, Jul. 1991; pp. 6368-6371.

Dawson, V. L. et al.; "Mechanisms of Nitric Oxide-Mediated Neurotoxicity in Primary Brain Cultures;" J. Neurosci., vol. 13, No. 6, Jun. 1993; pp. 2651-2661.

Dawson, V. L. et al.; "Resistance to Neurotoxicity in Cortical Cultures From Neuronal Nitric Oxide Synthase-Deficient Mice;" J. Neurosci., vol. 16, No. 8, Apr. 15, 1996; pp. 2479-2487.

Iadecola, C.; "Bright and Dark Sides of Nitric Oxide in Ischemic Brain Injury;" Trends Neurosci., vol. 20(3), 1997; pp. 132-139.

Huang, Z. et al.; Effects of Cerebral Ischemia in Mice Deficient in Neuronal Nitric Oxide Synthase; Science, vol. 265, Sep. 23, 1994; pp. 1883-1885.

Beckman, J. S. et al.; "Pathological Implications of Nitric Oxide, Superoxide and Peroxynitrite Formation;" Biochem. Soc. Trans., vol. 21, 1993; pp. 330-334.

Szabo, C. et al.; "DNA Strand Breakage, Activation of Poly(ADP-Ribose) Synthetase, and Cellular Energy Depletion Are Involved in the Cytotoxicity in Macrophages and Smooth Muscle Cells Exposed to Peroxynitrite;" Proc. Natl. Acad. Sci. USA, vol. 93, Mar. 1996; pp. 1753-1758.

Cristovao, L. et al.; "Effect of a Poly)ADP-Ribose) Polymerase Inhibitor on DNA Breakage and Cytotoxicity Induced by Hydrogen Peroxide and $^\gamma$-Radiation;" Teratogenesis, Carcinogenesis, and Mutagenesis, vol. 16, 1996; pp. 219-227.

Southan, G. J. et al.; "Spontaneous Rearrangement of Aminoalkylisothioureas Into Mercaptoalkylguanidines, A Novel Class of Nitric Oxide Synthase Inhibitors With Selectivity Towards the Inducible Isoform;" Br. J. Pharm., vol. 117, 1996; pp. 619-632.

Szabo, C. et al.; "Mercaptoethylguanidine and Guanidine Inhibitors of Nitric-Oxide Synthase React With Peroxynitrite and Protect Against Peroxynitrite-Induced Oxidative Damage;" J. Biol. Chem., vol. 272, No. 14, Apr. 4, 1997; pp. 9030-9036.

Szabo, C. et al.; "Protective Effect of an Inhibitor of Poly(ADP-Ribose) Synthetase in Collagen-Induced Arthritis;" Portland Press Proc., vol. 15, 1998; pp. 280-281.

Szabo, C.; "Role of Poly(ADP-Ribose) Synthetase in Inflammation;" European Journal of Pharmacology, vol. 350, No. 1, 1998; pp. 1-19.

Szabo, C. et al.; "Protection Against Peroxynitrite-Induced Fibroblast Injury and Arthritis Development by Inhibition of Poly(ADP-Ribose) Synthase;" Proc. Natl. Acad. Sci. USA, vol. 95, Mar. 1998; pp. 3867-3872.

Bauer, P. I. et al.; "Modification of Growth Related Enzymatic Pathways and Apparent Loss of Tumorigenicity of a Ras-Transformed Bovine Endothelial Cell Line by Treatment With 5-iodo-6-amino-1,2-benzopyrone (INH2BP);" Intl. J. Oncol., vol. 8;1996; pp. 239-252.

Hughes, C. et al.; "Induction of T Helper Cell Hyporesponsiveness in an Experimental Model of Autoimmunity by Using Nonmitogenic Anti-CD3 Monoclonal Antibody;" J. Immuno., vol. 153, 1994; pp. 3319-3325.

Salzman, A. L. et al., "Role of Peroxynitrite and Poly (ADP-Ribose) Synthase Activation Experimental Colitis;" Japanese J. Pharm., vol. 75 (Supp. I), 1997; p. 15.

Szabo, C. et al.; "Protective Effect of an Inhibitor of Poly (ADP-Ribose) Synthetase in Collagen-Induced Arthritis;" Japanese J. Pharm., vol. 75 (Supp. I), 1997; p. 102.

Saldeen, J. et al.; "Nicotinamide-Induced Apoptosis in Insulin Producing Cells Is Associated With Cleavage of Poly(ADP-Ribose) Polymerase;" Mol. Cellular Endocrinol., vol. 139, 1998; pp. 99-107.

Pieper, A. A. et al.; "Poly(ADP-Ribose) Polymerase, Nitric Oxide and Cell Death;" Trends in Pharmacological Sciences, vol. 20, 1999; pp. 171-181 (11 pages).

Burkart, V. et al.; "Mice Lacking the Poly(ADP-Ribose) Polymerase Gene Are Resistant to Pancreatic Beta-Cell Destruction and Diabetes Development Induced by Streptozocin;" Nature Medicine, vol. 5, No. 3, Mar. 1999; pp. 314-319.

Zingarelli, B. et al.; "Protective Effects of Nicotinamide Against Nitric Oxide-Mediated Delayed Vascular Failure in Endotoxic Shock: Potential Involvement of polyADP Ribosyl Synthetase;" Shock, vol. 5, No. 4, Apr. 1996; pp. 258-264.

Cuzzocrea, S. et al.; "Role of Peroxynitrite and Activation of Poly (ADP-Ribose) Synthetase in the Vascular Failure Induced by Zymosan-Activated Plasma;" Brit. J. Pharm., vol. 122, 1997; pp. 493-503.

Weltin, D. et al.; "Effect of 6(5H)-Phenanthridinone, An Inhibitor of Poly(ADP-Ribose) Polymerase, on Cultured Tumor Cells;" Oncology Research, vol. 6, No. 9, 1994; pp. 399-403.

Mao, J. et al.; "The Inhibition of Nitric Oxide-Activated Poly(ADP-Ribose) Synthetase Attenuates Transsynaptic Alteration of Spinal Cord Dorsal Horn Neurons and Neuropathic Pain in the Rat;" Pain, vol. 72, 1997; pp. 355-366.

Banasik, M. et al.; "Specific Inhibitors of Poly(ADP-Ribose) Synthetase and Mono(ADP-Ribosyl)transferase;" J. Biol. Chem., vol. 267, No. 3, 1992; pp. 1569-1575.

Griffin, R. J. et al.; "Novel Potent Inhibitors of the DNA Repair Enzyme Poly(ADPRibose)Polymerase (PARP);" Anti-Cancer Drug Design, vol. 10, 1995; pp. 507-514.

(56) References Cited

OTHER PUBLICATIONS

Suto, M. J. et al.; "Dihydroisoquinolinones: The Design and Synthesis of a New Series of Potent Inhibitors of Poly(ADP-Ribose) Polymerase;" Anti-Cancer Drug Design, vol. 7, 1991; pp. 107-117.
Griffin, R. J. et al.; "Resistance-Modifying Agents. 5. Synthesis and Biological Properties of Quinazolinone Inhibitors of the DNA Repair Enzyme Poly(ADP-Ribose) Polymerase (PARP);" J. Med. Chem., vol. 41, 1998; pp. 5247-5256.
Milam, K. M. et al.; "Inhibitors of Poly(Adenosine Diphosphate-Ribose) Synthesis: Effect on Other Metabolic Processes;" Science, vol. 223, Feb. 10, 1984; pp. 589-591.
Chadwick, B. P. et al.; "Histone H2A Variants and the Inactive X Chromosome: Identification of a Second MacroH2A Variant" Human Molecular Genetics, vol. 10, No. 10, 2001; pp. 1101-1113.
Costanzi, C. et al.; "Histone MacroH2A1 Is Concentrated in the Inactive X Chromosome of Female Mammals;" Nature, vol. 393, Jun. 11, 1998; pp. 599-601.
Zhang, R. et al.; "Formation of MacroH2A-Containing Senescence-Associated Heterochromatin Foci and Senescence Driven by ASF1a and HIRA;" Developemental Cell, vol. 8, Jan. 2005; pp. 19-30.
Grigoryev, S. A. et al.; "Dynamic Relocation of Epigenetic Chromatin Markers Reveals an Active Role of Constitutive Heterochromatin in the Transition From Proliferation to Quiescence;" Journal of Cell Science, vol. 117, No. 25, 2004; pp. 6153-6162.
Pehrson, J. R. et al.; "Evolutionary Conservation of Histone MacroH2A Subtypes and Domains;" Nucleic Acids Research, vol. 26, No. 12, 1998; , pp. 2837-2848.
Luger, K. et al.: "Crystal Structure of the Nucleosome Core Particle At 2.8 Å Resolution;" Nature, vol. 389 (6648), Sep. 18, 1997; pp. 251-260.
Tulin, A. et al.; "Chromatin Loosening by Poly(ADP)-Ribose Polymerase (PARP) At *Drosophila* Puff Loci;" Science, vol. 299, Jan. 24, 2003; , pp. 560-562.
Nasr, F. et al.; "Characterization of the *Saccharomyces cerevisiae* Cyclic Nucleotide Phosphodiesterase Involved in the Metabolism of ADP-Ribose 1", 2"-Cyclic Phosphate;" Nucleic Acids Research, vol. 28, No. 8, 2000; pp. 1676-1683.
Hofmann, A. et al.; "Structure and Mechanism of Activity of the Cyclic Phosphodiesterase of Appr>p, A Product of the tRNA;" The EMBO Journal, vol. 19, No. 22, 2000; pp. 6207-6217.
Duband-Goulet, I et al.; "Methods for Chromatin Assembly and Remodeling;" Methods, vol. 33(1), 2004; pp. 12-17.
English translation of Notice of Reasons for Rejection mailed Aug. 28, 2012 in corresponding Japanese Patent Application No. 2008-539534.
Lee et al., Isolation of cDNA clones encoding human histone macroH2A1 subtypes, Biochimica et Biophysica Acta, (1998) 1399(1):73-77.

\* cited by examiner

| | | | | |
|---|---|---|---|---|
| Sc. CPDase | 1——————— | ³⁹HVTV———————— | ¹⁵⁰HVSL——————————— | ²⁴⁰ |
| At. CPDase | 1——————— | ⁴³HVTV———————— | ¹¹⁹HLSL——————————— | ¹⁸² |
| Hs. CPDase | 1——————— | ²⁵²HCTT———————— | ³³¹HITL——————————— | ⁴²² |
| Hs. mH2A1.1 | 1——————— | ²¹³HPTN———————— | ²⁷¹HCNS——————————— | ³⁷⁰ |
| Hs. mH2A1.2 | 1——————— | ²¹⁶NPTN———————— | ²⁷⁴HCNS——————————— | ³⁷³ |
| Hs. mH2A2 | 1——————— | ²¹⁶HPTT———————— | ²⁷⁴HCHI——————————— | ³⁷³ |
| Hs. mH2A1.1-mut | 1——————— | ²¹³AAAA———————— | ²⁷³HCNS——————————— | ³⁷⁰ |
| Consensus | | ————————HXTX———— | ————————HXTX——————— | |
| | | | S | |
| | | | N | |
| | | | H | |

Figure 16

SEQUENCE LISTING

<160> NUMBER OF SEQ ID NOS: 35

<210> SEQ ID NO 1
<211> LENGTH: 369
<212> TYPE: PRT
<213> ORGANISM: Homo sapiens

<400> SEQUENCE: 1

| | | | | | | | | | | | | | | |
|---|---|---|---|---|---|---|---|---|---|---|---|---|---|---|
|Met|Ser|Ser|Arg|Gly|Gly|Lys|Lys|Ser|Thr|Lys|Thr|Ser|Arg|Ser|
|1| | | |5| | | | |10| | | | |15|
|Ala|Lys|Ala|Gly|Val|Ile|Phe|Pro|Val|Gly|Arg|Met|Leu|Arg|Tyr|Ile|
| | | |20| | | | |25| | | | |30| |
|Lys|Lys|Gly|His|Pro|Lys|Tyr|Arg|Ile|Gly|Val|Gly|Ala|Pro|Val|Tyr|
| | | |35| | | | |40| | | | |45| |
|Met|Ala|Ala|Val|Leu|Glu|Tyr|Leu|Thr|Ala|Glu|Ile|Leu|Glu|Leu|Ala|
| |50| | | | |55| | | | |60| | | |
|Gly|Asn|Ala|Ala|Arg|Asp|Asn|Lys|Lys|Gly|Arg|Val|Thr|Pro|Arg|His|
|65| | | | |70| | | | |75| | | | |80|
|Ile|Leu|Leu|Ala|Val|Ala|Asn|Asp|Glu|Glu|Leu|Asn|Gln|Leu|Leu|Lys|
| | | | |85| | | | |90| | | | |95| |
|Gly|Val|Thr|Ile|Ala|Ser|Gly|Gly|Val|Leu|Pro|Asn|Ile|His|Pro|Glu|
| | | |100| | | | |105| | | | |110| |
|Leu|Leu|Ala|Lys|Lys|Arg|Gly|Ser|Lys|Gly|Lys|Leu|Glu|Ala|Ile|Ile|
| | | |115| | | | |120| | | | |125| |
|Thr|Pro|Pro|Pro|Ala|Lys|Lys|Ala|Lys|Ser|Pro|Ser|Gln|Lys|Lys|Pro|
| |130| | | | |135| | | | |140| | | |
|Val|Ser|Lys|Lys|Ala|Gly|Gly|Lys|Lys|Gly|Ala|Arg|Lys|Ser|Lys|Lys|
|145| | | | |150| | | | |155| | | | |160|
|Lys|Gln|Gly|Glu|Val|Ser|Lys|Ala|Ala|Ser|Ala|Asp|Ser|Thr|Thr|Glu|
| | | | |165| | | | |170| | | | |175| |
|Gly|Thr|Pro|Ala|Asp|Gly|Phe|Thr|Val|Leu|Ser|Thr|Lys|Ser|Leu|Phe|
| | | |180| | | | |185| | | | |190| |
|Leu|Gly|Gln|Lys|Leu|Gln|Val|Val|Gln|Ala|Asp|Ile|Ala|Ser|Ile|Asp|
| | | |195| | | | |200| | | | |205| |
|Ser|Asp|Ala|Val|Val|His|Pro|Thr|Asn|Thr|Asp|Phe|Tyr|Ile|Gly|Gly|
| |210| | | | |215| | | | |220| | | |
|Glu|Val|Gly|Asn|Thr|Leu|Glu|Lys|Lys|Gly|Gly|Lys|Glu|Phe|Val|Glu|
|225| | | | |230| | | | |235| | | | |240|
|Ala|Val|Leu|Glu|Leu|Arg|Lys|Lys|Asn|Gly|Pro|Leu|Glu|Val|Ala|Gly|
| | | | |245| | | | |250| | | | |255| |
|Ala|Ala|Val|Ser|Ala|Gly|His|Gly|Leu|Pro|Ala|Lys|Phe|Val|Ile|His|
| | | |260| | | | |265| | | | |270| |
|Cys|Asn|Ser|Pro|Val|Trp|Gly|Ala|Asp|Lys|Cys|Glu|Glu|Leu|Leu|Glu|
| | |275| | | | |280| | | | |285| | |
|Lys|Thr|Val|Lys|Asn|Cys|Leu|Ala|Leu|Ala|Asp|Asp|Lys|Lys|Leu|Lys|
| |290| | | | |295| | | | |300| | | |
|Ser|Ile|Ala|Phe|Pro|Ser|Ile|Gly|Ser|Gly|Arg|Asn|Gly|Phe|Pro|Lys|
|305| | | | |310| | | | |315| | | | |320|
|Gln|Thr|Ala|Ala|Gln|Leu|Ile|Leu|Lys|Ala|Ile|Ser|Ser|Tyr|Phe|Val|
| | | | |325| | | | |330| | | | |335| |
|Ser|Thr|Met|Ser|Ser|Ile|Lys|Thr|Val|Tyr|Phe|Val|Leu|Phe|Asp| |
| | | |340| | | | |345| | | | |350| | |
|Ser|Glu|Ser|Ile|Gly|Ile|Tyr|Val|Gln|Glu|Met|Ala|Lys|Leu|Asp|Ala|
| | | |355| | | | |360| | | | |365| | |
|Asn| | | | | | | | | | | | | | | |

<210> SEQ ID NO 2
<211> LENGTH: 371
<212> TYPE: PRT
<213> ORGANISM: Homo sapiens -continued

```
<400> SEQUENCE: 2

Met Ser Ser Arg Gly Gly Lys Lys Ser Thr Lys Thr Ser Arg Ser
1               5                   10                  15

Ala Lys Ala Gly Val Ile Phe Pro Val Gly Arg Met Leu Arg Tyr Ile
            20                  25                  30

Lys Lys Gly His Pro Lys Tyr Arg Ile Gly Val Gly Ala Pro Val Tyr
            35                  40                  45

Met Ala Ala Val Leu Glu Tyr Leu Thr Ala Glu Ile Leu Glu Leu Ala
    50                  55                  60

Gly Asn Ala Ala Arg Asp Asn Lys Lys Gly Arg Val Thr Pro Arg His
65                  70                  75                  80

Ile Leu Leu Ala Val Ala Asn Asp Glu Glu Leu Asn Gln Leu Leu Lys
                85                  90                  95

Gly Val Thr Ile Ala Ser Gly Gly Val Leu Pro Asn Ile His Pro Glu
            100                 105                 110

Leu Leu Ala Lys Lys Arg Gly Ser Lys Gly Lys Leu Glu Ala Ile Ile
        115                 120                 125

Thr Pro Pro Pro Ala Lys Lys Ala Lys Ser Pro Ser Gln Lys Lys Pro
    130                 135                 140

Val Ser Lys Lys Ala Gly Gly Lys Lys Gly Ala Arg Lys Ser Lys Lys
145                 150                 155                 160

Gln Gly Glu Val Ser Lys Ala Ser Ala Asp Ser Thr Thr Glu Gly
                165                 170                 175

Thr Pro Ala Asp Gly Phe Thr Val Leu Ser Thr Lys Ser Leu Phe Leu
            180                 185                 190

Gly Gln Lys Leu Asn Leu Ile His Ser Glu Ile Ser Asn Leu Ala Gly
        195                 200                 205

Phe Glu Val Glu Ala Ile Ile Asn Pro Thr Asn Ala Asp Ile Asp Leu
    210                 215                 220

Lys Asp Asp Leu Gly Asn Thr Leu Glu Lys Lys Gly Lys Glu Phe
225                 230                 235                 240

Val Glu Ala Val Leu Glu Leu Arg Lys Lys Asn Gly Pro Leu Glu Val
                245                 250                 255

Ala Gly Ala Ala Val Ser Ala Gly His Gly Leu Pro Ala Lys Phe Val
            260                 265                 270

Ile His Cys Asn Ser Pro Val Trp Gly Ala Asp Lys Cys Glu Glu Leu
        275                 280                 285

Leu Glu Lys Thr Val Lys Asn Cys Leu Ala Leu Ala Asp Asp Lys Lys
    290                 295                 300

Leu Lys Ser Ile Ala Phe Pro Ser Ile Gly Ser Gly Arg Asn Gly Phe
305                 310                 315                 320

Pro Lys Gln Thr Ala Ala Gln Leu Ile Leu Lys Ala Ile Ser Ser Tyr
                325                 330                 335

Phe Val Ser Thr Met Ser Ser Ser Ile Lys Thr Val Tyr Phe Val Leu
            340                 345                 350

Phe Asp Ser Glu Ser Ile Gly Ile Tyr Val Gln Glu Met Ala Lys Leu
        355                 360                 365

Asp Ala Asn
    370

<210> SEQ ID NO 3
<211> LENGTH: 372
<212> TYPE: PRT
<213> ORGANISM: Homo sapiens
```

```
<400> SEQUENCE: 3

Met Ser Gly Arg Ser Gly Lys Lys Met Ser Lys Leu Ser Arg Ser
1               5                   10                  15

Ala Arg Ala Gly Val Ile Phe Pro Val Gly Arg Leu Met Arg Tyr Leu
            20                  25                  30

Lys Lys Gly Thr Phe Lys Tyr Arg Ile Ser Val Gly Ala Pro Val Tyr
        35                  40                  45

Met Ala Ala Val Ile Glu Tyr Leu Ala Ala Glu Ile Leu Glu Leu Ala
50                  55                  60

Gly Asn Ala Ala Arg Asp Asn Lys Lys Ala Arg Ile Ala Pro Arg His
65                  70                  75                  80

Ile Leu Leu Ala Val Ala Asn Asp Glu Glu Leu Asn Gln Leu Leu Lys
                85                  90                  95

Gly Val Thr Ile Ala Ser Gly Gly Val Leu Pro Arg Ile His Pro Glu
            100                 105                 110

Leu Leu Ala Lys Lys Arg Gly Thr Lys Gly Lys Ser Glu Thr Ile Leu
        115                 120                 125

Ser Pro Pro Glu Lys Arg Gly Arg Lys Ala Thr Ser Gly Lys Lys
130                 135                 140

Gly Gly Lys Lys Ser Lys Ala Ala Lys Pro Arg Thr Ser Lys Lys Ser
145                 150                 155                 160

Lys Pro Lys Asp Ser Asp Lys Glu Gly Thr Ser Asn Ser Thr Ser Glu
                165                 170                 175

Asp Gly Pro Gly Asp Gly Phe Thr Ile Leu Ser Ser Lys Ser Leu Val
            180                 185                 190

Leu Gly Gln Lys Leu Ser Leu Thr Gln Ser Asp Ile Ser His Ile Gly
        195                 200                 205

Ser Met Arg Val Glu Gly Ile Val His Pro Thr Thr Ala Glu Ile Asp
210                 215                 220

Leu Lys Glu Asp Ile Gly Lys Ala Leu Glu Lys Ala Gly Gly Lys Glu
225                 230                 235                 240

Phe Leu Glu Thr Val Lys Glu Leu Arg Lys Ser Gln Gly Pro Leu Glu
                245                 250                 255

Val Ala Glu Ala Ala Val Ser Gln Ser Ser Gly Leu Ala Ala Lys Phe
            260                 265                 270

Val Ile His Cys His Ile Pro Gln Trp Gly Ser Asp Lys Cys Glu Glu
        275                 280                 285

Gln Leu Glu Glu Thr Ile Lys Asn Cys Leu Ser Ala Ala Glu Asp Lys
290                 295                 300

Lys Leu Lys Ser Val Ala Phe Pro Pro Phe Pro Ser Gly Arg Asn Cys
305                 310                 315                 320

Phe Pro Lys Gln Thr Ala Ala Gln Val Thr Leu Lys Ala Ile Ser Ala
                325                 330                 335

His Phe Asp Asp Ser Ser Ala Ser Ser Leu Lys Asn Val Tyr Phe Leu
            340                 345                 350

Leu Phe Asp Ser Glu Ser Ile Gly Ile Tyr Val Gln Glu Met Ala Lys
        355                 360                 365

Leu Asp Ala Lys
    370

<210> SEQ ID NO 4
<211> LENGTH: 1890
<212> TYPE: DNA
<213> ORGANISM: Homo sapiens
```

<400> SEQUENCE: 4

```
gcgccgggcg aggggggaga gcgcgggccg cgcgggcggg aagcgaagag gcgggcgggc       60
cagcgaggag cgcggagaga aaaggcgcga gcggccagga gggctcaggc cgagacacct      120
tgcagctgcc gccgccgcca ccgagccgcc gctgtgctca ctgatccgcc tccagggcca      180
ccgccatgtc gagccgcggt gggaagaaga agtccaccaa gacgtccagg tctgccaaag      240
caggagtcat ctttcccgtg gggcggatgc tgcggtacat caagaaaggc cacccccaagt     300
acaggattgg agtgggggca cccgtgtaca tggccgccgt cctggaatac ctgacagcgg      360
agattctgga gctggctggc aatgcagcga gagacaacaa gaagggacgg gtcacacccc      420
ggcacatcct gctggctgtg gccaatgatg aagagctgaa tcagctgcta aaaggagtca      480
ccatagccag tggggtgtgt tacccaaca tccaccccga gttgctagcg aagaagcggg       540
gatccaaagg aaagttggaa gccatcatca caccaccccc agccaaaaag gccaagtctc      600
catcccagaa gaagcctgta tctaaaaaag caggaggcaa gaaggggcc cggaaatcca       660
agaagaagca gggtgaagtc agtaaggcag ccagcgccga cagcacaacc gagggcacac      720
ctgccgacgg cttcacagtc ctctccacca gagcctctt ccttggccag aagttgcaag       780
ttgtacaggc tgacattgcc tcgatcgaca gtgatgctgt cgttcacccg acaaacactg      840
acttctacat cggtggtgaa gtaggaaaca cgctggagaa gaaggtggc aaggagtttg       900
tggaagctgt cctggaactc cggaaaaaga acgggcccttt ggaagtagct ggagctgctg     960
tcagcgcagg ccatggcctg cctgccaagt tgtgatccca ctgtaatagt ccagtttggg     1020
gtgcagacaa gtgtgaagaa cttctggaaa agacagtgaa aaactgcttg gccctggctg     1080
atgataagaa gctgaaatcc attgcatttc catccatcgg cagcggcagg aacggttttc     1140
caaagcagac agcagctcag ctgattctga aggccatctc cagttacttc gtgtctacaa     1200
tgtcctcttc catcaaaacg gtgtacttcg tgcttttga cagcgagagt ataggcatct     1260
atgtgcagga aatggccaag ctggacgcca actaggctga gcaatgacag aaccagctgc     1320
accatgtacc ccaccttcag ttttaaagaa aaaaaaaatc cccttcactc ctactgggag     1380
gtgggacccc tttcatttc agtttttgctc atctagggaa aataaggctt tggttttccag    1440
tttaattgtt tttgaccttc taaaatgttt ttatgttagc actgatagtt ggcattactg     1500
ttgttaagca ctgtgttcca gaccgtgtct gacttagtgt aacctaggag attttatagt     1560
tttatttaa tgaaaccctg attgacgcac agcagtgggg agaacagcgt ctttttacctg     1620
tcaccgaagc caggaagccc cgtttgtaag cgtgtgttgt ggtgctttat tgtacatcct     1680
ccagtggcgt tcttttttact ctaatgttct tttggtttcc ccctcagaa gaatcatgaa     1740
tttgcaacag acctaatttt tggttacttt ttgtcttatt gatggatttg aaaatgaaag     1800
atttaataag gcaaagcaga atctgttgtc cttaattata tttgcaattt ggaatttgtg     1860
tgagttgatt tagtaaaatg ttaaaccgtt                                      1890
```

<210> SEQ ID NO 5
<211> LENGTH: 1923
<212> TYPE: DNA
<213> ORGANISM: Homo sapiens

<400> SEQUENCE: 5

```
gactgtctac attagtaatt cccaacttgg gtccgaaagt gaactttgc tgaagcgaag        60
tagctaaccg cttccatgtg caaggcaggt tccagacttc ggggtgagga ggattaactg      120
aaggacccca ggggaaccgg tgtgctcact gatccgcctc cagggccacc gccatgtcga     180
```

```
gccgcggtgg gaagaagaag tccaccaaga cgtccaggtc tgccaaagca ggagtcatct    240
ttcccgtggg gcggatgctg cggtacatca agaaaggcca ccccaagtac aggattggag    300
tgggggcacc cgtgtacatg gccgccgtcc tggaatacct gacagcggag attctggagc    360
tggctggcaa tgcagcgaga gacaacaaga agggacgggt cacaccccgg cacatcctgc    420
tggctgtggc caatgatgaa gagctgaatc agctgctaaa aggagtcacc atagccagtg    480
ggggtgtgtt acccaacatc caccccgagt tgctagcgaa gaagcgggga tccaaaggaa    540
agttggaagc catcatcaca ccaccccag ccaaaaaggc caagtctcca tcccagaaga    600
agcctgtatc taaaaaagca ggaggcaaga aggggcccg aaatccaag aagcagggtg    660 aagtcagtaa ggcagccagc gccgacagca caaccgaggg cacacctgcc gacggcttca    720
cagtcctctc caccaagagc ctcttccttg ccagaagct gaaccttatt cacagtgaaa    780
tcagtaattt agccggcttt gaggtggagg ccataatcaa tcctaccaat gctgacattg    840
accttaaaga tgacctagga aacacgctgg agaagaaagg tggcaaggag tttgtggaag    900
ctgtcctgga actccggaaa aagaacgggc ccttggaagt agctggagct gctgtcagcg    960
caggccatgg cctgcctgcc aagtttgtga tccactgtaa tagtccagtt tggggtgcag   1020
acaagtgtga agaacttctg gaaaagacag tgaaaaactg cttggccctg gctgatgata   1080
agaagctgaa atccattgca tttccatcca tcggcagcgg caggaacggt tttccaaagc   1140
agacagcagc tcagctgatt ctgaaggcca ctctccagtta cttcgtgtct acaatgtcct   1200
cttccatcaa aacggtgtac ttcgtgcttt ttgacagcga gagtataggc atctatgtgc   1260
aggaaatggc caagctggac gccaactagg ctgagcaatg acagaaccag ctgcaccatg   1320
taccccacct tcagttaaa agaaaaaaaa aatcccttc actcctactg ggaggtggga   1380 ccccttcat tttcagtttt gctcatctag ggaaaataag gctttggttt ccagtttaat   1440 tgttttgac cttctaaaat gttttatgt tagcactgat agttggcatt actgttgtta   1500
agcactgtgt tccagaccgt gtctgactta gtgtaaccta ggagatttta tagttttatt   1560
ttaatgaaac cctgattgac gcacagcagt ggggagaaca gcgtctttta cctgtcaccg   1620
aagccaggaa gccccgtttg taagcgtgtg ttgtggtgct ttattgtaca tcctccagtg   1680
gcgttctttt tactctaatg ttcttttggt ttccccctc agaagaatca tgaatttgca   1740
acagacctaa ttttggtta ctttttgtct tattgatgga tttgaaaatg aaagatttaa   1800
taaggcaaag cagaatctgt tgtccttaat tatatttgca atttggaatt tgtgtgagtt   1860
gatttagtaa aatgttaaac cgttaaaaaa aaaaaaaaa aaaaaaaaaa aaaaaaaaaa   1920
aaa                                                                 1923

<210> SEQ ID NO 6
<211> LENGTH: 1932
<212> TYPE: DNA
<213> ORGANISM: Homo sapiens

<400> SEQUENCE: 6
aagcttggca cgaggccgcc attgacacgc acagatagaa cccaaagaaa ggcaaagagt     60
cctgcccggc accggcgccg cgtgggccaa acctgcgccc gtggaggggc gcgcagaggg    120
caccgggcgc cgggagcagg cggcgcagca ccagcattgt gttagtgccg ggaggccact    180
gtgtcagcaa gctgagaggg aaactgaagc aagatgtcgg gccggagtgg gaagaagaaa    240
atgtccaagc tgtcccgttc agctagggca ggtgtcatct ttccagtggg gaggctgatg    300
cgttatctga agaaagggac gttcaagtac cggatcagcg tgggcgcccc tgtctacatg    360
```

```
gcggcagtca ttgagtacct ggcagcggaa attctagaat tggccggcaa tgccgcgagg      420
gacaacaaga aggcccggat agccccgaga cacatcttgc tggcagttgc caatgacgag      480
gagctcaacc agctgctaaa aggagtgacc atcgccagtg gaggcgtcct gcccagaatt      540
caccccgaac tgctggccaa aaagcgaggg accaaaggca agtcggaaac gatcctctcc      600 ccaccccag agaaaagagg caggaaggcc acgtcaggca agaaggggg gaagaaatcc        660 aaggctgcca accacggac gtccaaaaag tccaaaccaa aggacagcga taaagaagga      720
acttcaaatt ccacctctga agatgggcca ggggatggat tcaccattct gtcttctaag      780
agccttgttc tgggacagaa gctgtcctta acccagagtg catcagcca tattggctcc      840 atgagagtgg agggcattgt ccacccaacc acagccgaaa ttgacctcaa agaagatata     900
ggtaaagcct tggaaaagcc tgggggaaaa gagttcttgg aaacggtaaa ggagcttcgc     960
aaatcccaag gccctttgga agtcgccgaa gccgccgtca gccaatccag tggactcgca    1020
gccaaatttg tcatccactg tcacatccct cagtggggct ccgacaaatg tgaagaacag    1080
cttgaagaga ccatcaaaaa ctgcctgtca gcggcggagg acaagaagct aaagtccgtc    1140
gcgttcccgc cttccccag cggcagaaac tgctttccca aacagactgc ggcccaggtg      1200
accctcaaag ccatctcagc ccactttgat gactcgagcg cgtcctcgct gaagaacgtg    1260
tacttcctgc tcttcgacag cgagagcatc ggcatctacg tgcaggagat ggccaagctc    1320
gacgccaagt agccgccgca cttccagca gggatcggag gacgacccga gtcccaagag      1380
tggggttttg cttttaaaa ggagagagga ggggtgatgg caggggagtg gagggtggcc      1440
gggcaggtcc tgccggcgca gggagccctc tgcccttcac actctcctcc aaaagagcct    1500
ccatctgtaa ggaagcaggt ctccgcgagg ggtttctttc catgtgtttt cctcctgttg    1560
ttaaaagaac tttttaaaa aaacagacct cgttttagat ttatagcatt gactttaca      1620 cacattcaca caagaaaaaa atcctttcaa aattcttaaa tcttctgttc ctccttttc     1680 caagggaaga gggcaaaaag tggcctgggc tctgttggtg tgcgtgttcc gtggcggaga    1740
gaagaaaatg ggaaagacat ctcactggtg ctttctctt tgttttagt gccccccgcc      1800 cccatccta taatatctgt aactactcct aaaaaggttt tgattcaggc ttttttttgg     1860
tttcattttg tttttttaag aaaagaaaa tgaaggaaa aaaaaaaaaa aaaaaaaat       1920 tcctgcggcc gc                                                        1932

<210> SEQ ID NO 7
<211> LENGTH: 8
<212> TYPE: PRT
<213> ORGANISM: Artificial
<220> FEATURE:
<223> OTHER INFORMATION: FLAG Peptide

<400> SEQUENCE: 7

Asp Tyr Lys Asp Asp Asp Asp Lys
1               5

<210> SEQ ID NO 8
<211> LENGTH: 9
<212> TYPE: PRT
<213> ORGANISM: Artificial
<220> FEATURE:
<223> OTHER INFORMATION: HA peptide

<400> SEQUENCE: 8

Tyr Pro Tyr Asp Val Pro Asp Tyr Ala
1               5
```

```
<210> SEQ ID NO 9
<211> LENGTH: 25
<212> TYPE: DNA
<213> ORGANISM: Artificial
<220> FEATURE:
<223> OTHER INFORMATION: hsp70-1 primer

<400> SEQUENCE: 9
ggcgaaaccc ctggaatatt cccga                                        25

<210> SEQ ID NO 10
<211> LENGTH: 19
<212> TYPE: DNA
<213> ORGANISM: Artificial
<220> FEATURE:
<223> OTHER INFORMATION: HSP primer

<400> SEQUENCE: 10
agccttggga caacgggag                                               19

<210> SEQ ID NO 11
<211> LENGTH: 22
<212> TYPE: DNA
<213> ORGANISM: Artificial
<220> FEATURE:
<223> OTHER INFORMATION: HSP primer

<400> SEQUENCE: 11
caggtgatca acgacggaga ca                                           22

<210> SEQ ID NO 12
<211> LENGTH: 22
<212> TYPE: DNA
<213> ORGANISM: Artificial
<220> FEATURE:
<223> OTHER INFORMATION: HSP primer

<400> SEQUENCE: 12
gtcgatcgtc aggatggaca cg                                           22

<210> SEQ ID NO 13
<211> LENGTH: 22
<212> TYPE: DNA
<213> ORGANISM: Artificial
<220> FEATURE:
<223> OTHER INFORMATION: GAPDH primer

<400> SEQUENCE: 13
ggacctgacc tgccgtctag aa                                           22

<210> SEQ ID NO 14
<211> LENGTH: 22
<212> TYPE: DNA
<213> ORGANISM: Artificial
<220> FEATURE:
<223> OTHER INFORMATION: GAPDH primer

<400> SEQUENCE: 14
ggtgtcgctg ttgaagtcag ag                                           22

<210> SEQ ID NO 15
<211> LENGTH: 20
<212> TYPE: RNA
<213> ORGANISM: Artificial
<220> FEATURE:
<223> OTHER INFORMATION: macroH2A1 siRNA
```

<400> SEQUENCE: 15
aagcagggug aagucaguaa                                                                      20

<210> SEQ ID NO 16
<211> LENGTH: 21
<212> TYPE: RNA
<213> ORGANISM: Artificial
<220> FEATURE:
<223> OTHER INFORMATION: PARP1 siRNA

<400> SEQUENCE: 16
aagccuccgc uccugaacaa u                                                                    21

<210> SEQ ID NO 17
<211> LENGTH: 21
<212> TYPE: DNA
<213> ORGANISM: Artificial
<220> FEATURE:
<223> OTHER INFORMATION: Scrambled control siRNA

<400> SEQUENCE: 17
caugucaugu ucacaucuct t                                                                    21

<210> SEQ ID NO 18
<211> LENGTH: 249
<212> TYPE: PRT
<213> ORGANISM: Artificial
<220> FEATURE:
<223> OTHER INFORMATION: Macro domain of macroH2A1.1

<400> SEQUENCE: 18

Lys Gly Lys Leu Glu Ala Ile Ile Thr Pro Pro Ala Lys Lys Ala
1               5                   10                  15

Lys Ser Pro Ser Gln Lys Lys Pro Val Ser Lys Ala Gly Gly Lys
            20                  25                  30

Lys Gly Ala Arg Lys Ser Lys Lys Lys Gln Gly Glu Val Ser Lys Ala
        35                  40                  45

Ala Ser Ala Asp Ser Thr Thr Glu Gly Thr Pro Ala Asp Gly Phe Thr
    50                  55                  60

Val Leu Ser Thr Lys Ser Leu Phe Leu Gly Gln Lys Leu Gln Val Val
65                  70                  75                  80

Gln Ala Asp Ile Ala Ser Ile Asp Ser Asp Ala Val Val His Pro Thr
                85                  90                  95

Asn Thr Asp Phe Tyr Ile Gly Gly Glu Val Gly Asn Thr Leu Glu Lys
            100                 105                 110

Lys Gly Gly Lys Glu Phe Val Glu Ala Val Leu Glu Leu Arg Lys Lys
        115                 120                 125

Asn Gly Pro Leu Glu Val Ala Gly Ala Ala Val Ser Ala Gly His Gly
    130                 135                 140

Leu Pro Ala Lys Phe Val Ile His Cys Asn Ser Pro Val Trp Gly Ala
145                 150                 155                 160

Asp Lys Cys Glu Glu Leu Leu Glu Lys Thr Val Lys Asn Cys Leu Ala
                165                 170                 175

Leu Ala Asp Asp Lys Lys Leu Lys Ser Ile Ala Phe Pro Ser Ile Gly
            180                 185                 190

Ser Gly Arg Asn Gly Phe Pro Lys Gln Thr Ala Ala Gln Leu Ile Leu
        195                 200                 205

Lys Ala Ile Ser Ser Tyr Phe Val Ser Thr Met Ser Ser Ser Ile Lys
    210                 215                 220

Thr Val Tyr Phe Val Leu Phe Asp Ser Glu Ser Ile Gly Ile Tyr Val
225                 230                 235                 240

Gln Glu Met Ala Lys Leu Asp Ala Asn
            245

<210> SEQ ID NO 19
<211> LENGTH: 251
<212> TYPE: PRT
<213> ORGANISM: Artificial
<220> FEATURE:
<223> OTHER INFORMATION: Macro domain of macroH2A1.2

<400> SEQUENCE: 19

Lys Gly Lys Leu Glu Ala Ile Ile Thr Pro Pro Ala Lys Lys Ala
1               5                   10                  15

Lys Ser Pro Ser Gln Lys Lys Pro Val Ser Lys Lys Ala Gly Gly Lys
            20                  25                  30

Lys Gly Ala Arg Lys Ser Lys Lys Gln Gly Glu Val Ser Lys Ala Ala
            35                  40                  45

Ser Ala Asp Ser Thr Thr Glu Gly Thr Pro Ala Asp Gly Phe Thr Val
        50                  55                  60

Leu Ser Thr Lys Ser Leu Phe Leu Gly Gln Lys Leu Asn Leu Ile His
65                  70                  75                  80

Ser Glu Ile Ser Asn Leu Ala Gly Phe Glu Val Glu Ala Ile Ile Asn
                85                  90                  95

Pro Thr Asn Ala Asp Ile Asp Leu Lys Asp Asp Leu Gly Asn Thr Leu
            100                 105                 110

Glu Lys Lys Gly Gly Lys Glu Phe Val Glu Ala Val Leu Glu Leu Arg
            115                 120                 125

Lys Lys Asn Gly Pro Leu Glu Val Ala Gly Ala Ala Val Ser Ala Gly
        130                 135                 140

His Gly Leu Pro Ala Lys Phe Val Ile His Cys Asn Ser Pro Val Trp
145                 150                 155                 160

Gly Ala Asp Lys Cys Glu Glu Leu Leu Glu Lys Thr Val Lys Asn Cys
                165                 170                 175

Leu Ala Leu Ala Asp Asp Lys Lys Leu Lys Ser Ile Ala Phe Pro Ser
            180                 185                 190

Ile Gly Ser Gly Arg Asn Gly Phe Pro Lys Gln Thr Ala Ala Gln Leu
            195                 200                 205

Ile Leu Lys Ala Ile Ser Ser Tyr Phe Val Ser Thr Met Ser Ser Ser
        210                 215                 220

Ile Lys Thr Val Tyr Phe Val Leu Phe Asp Ser Glu Ser Ile Gly Ile
225                 230                 235                 240

Tyr Val Gln Glu Met Ala Lys Leu Asp Ala Asn
                245                 250

<210> SEQ ID NO 20
<211> LENGTH: 252
<212> TYPE: PRT
<213> ORGANISM: Artificial
<220> FEATURE:
<223> OTHER INFORMATION: Macro domain of macroH2A2

<400> SEQUENCE: 20

Lys Gly Lys Ser Glu Thr Ile Leu Ser Pro Pro Glu Lys Arg Gly
1               5                   10                  15

Arg Lys Ala Thr Ser Gly Lys Lys Gly Gly Lys Lys Ser Lys Ala Ala
            20                  25                  30

```
Lys Pro Arg Thr Ser Lys Lys Ser Lys Pro Lys Asp Ser Asp Lys Glu
            35                  40                  45

Gly Thr Ser Asn Ser Thr Ser Glu Asp Gly Pro Gly Asp Gly Phe Thr
 50                  55                  60

Ile Leu Ser Ser Lys Ser Leu Val Leu Gly Gln Lys Leu Ser Leu Thr
 65                  70                  75                  80

Gln Ser Asp Ile Ser His Ile Gly Ser Met Arg Val Glu Gly Ile Val
                 85                  90                  95

His Pro Thr Thr Ala Glu Ile Asp Leu Lys Glu Asp Ile Gly Lys Ala
                100                 105                 110

Leu Glu Lys Ala Gly Gly Lys Glu Phe Leu Glu Thr Val Lys Glu Leu
            115                 120                 125

Arg Lys Ser Gln Gly Pro Leu Glu Val Ala Glu Ala Val Ser Gln
130                 135                 140

Ser Ser Gly Leu Ala Ala Lys Phe Val Ile His Cys His Ile Pro Gln
145                 150                 155                 160

Trp Gly Ser Asp Lys Cys Glu Glu Gln Leu Glu Thr Ile Lys Asn
                165                 170                 175

Cys Leu Ser Ala Ala Glu Asp Lys Lys Leu Lys Ser Val Ala Phe Pro
                180                 185                 190

Pro Phe Pro Ser Gly Arg Asn Cys Phe Pro Lys Gln Thr Ala Gln
            195                 200                 205

Val Thr Leu Lys Ala Ile Ser Ala His Phe Asp Asp Ser Ser Ala Ser
210                 215                 220

Ser Leu Lys Asn Val Tyr Phe Leu Leu Phe Asp Ser Glu Ser Ile Gly
225                 230                 235                 240

Ile Tyr Val Gln Glu Met Ala Lys Leu Asp Ala Lys
                245                 250

<210> SEQ ID NO 21
<211> LENGTH: 57
<212> TYPE: PRT
<213> ORGANISM: Artificial
<220> FEATURE:
<223> OTHER INFORMATION: Macro domain of AF1521

<400> SEQUENCE: 21

Gln Gly Asp Ile Thr Gln Tyr Pro Ala Lys Ala Ile Val Asn Ala Ala
1               5                   10                  15

Asn Lys Arg Leu Glu His Gly Gly Gly Val Ala Lys Tyr Val Phe His
            20                  25                  30

Thr Val Gly Pro Ile Ala Glu Glu Met Gly Val Glu Ser Ile Ala Phe
        35                  40                  45

Pro Ala Val Ser Ala Gly Ile Tyr Gly
    50                  55

<210> SEQ ID NO 22
<211> LENGTH: 57
<212> TYPE: PRT
<213> ORGANISM: Artificial
<220> FEATURE:
<223> OTHER INFORMATION: Macro domain of NP_598908

<400> SEQUENCE: 22

Arg Gly Asp Ile Thr Lys Leu Glu Val Asp Ala Ile Val Asn Ala Ala
1               5                   10                  15

Asn Ser Ser Leu Leu Gly Gly Gly Gly Val Asp Lys Tyr Val Ile His
            20                  25                  30
```

```
Thr Val Gly Pro Ile Leu Leu Glu His Arg Leu Arg Ser Val Ala Phe
        35                  40                  45

Pro Cys Ile Ser Thr Gly Val Phe Gly
    50                  55

<210> SEQ ID NO 23
<211> LENGTH: 59
<212> TYPE: PRT
<213> ORGANISM: Artificial
<220> FEATURE:
<223> OTHER INFORMATION: Macro domain of YBR022WP

<400> SEQUENCE: 23

Lys Gly Asn Ile Leu Lys Pro Lys Ser Tyr Ala Arg Ile Leu Ile His
1               5                   10                  15

Ser Cys Asn Cys Asn Gly Ser Trp Gly Gly Gly Ile Ala Leu Leu Ile
            20                  25                  30

Cys Cys Leu Phe Thr Ser Ser Lys Leu Lys Thr Phe Arg Glu Ala Lys
        35                  40                  45

Asp Lys Thr Arg Thr Ser Glu Asp Ser Ile Gly
    50                  55

<210> SEQ ID NO 24
<211> LENGTH: 22
<212> TYPE: DNA
<213> ORGANISM: Artificial Sequence
<220> FEATURE:
<223> OTHER INFORMATION: hsp70-2 primer

<400> SEQUENCE: 24
ggccgagagt cagggaggaa cc                                      22

<210> SEQ ID NO 25
<211> LENGTH: 21
<212> TYPE: DNA
<213> ORGANISM: Artificial Sequence
<220> FEATURE:
<223> OTHER INFORMATION: hsp70-2 primer

<400> SEQUENCE: 25
actcttccag ctccaccaca g                                       21

<210> SEQ ID NO 26
<211> LENGTH: 22
<212> TYPE: DNA
<213> ORGANISM: Artificial Sequence
<220> FEATURE:
<223> OTHER INFORMATION: hsp70-8 primer

<400> SEQUENCE: 26
tgtggcttcc ttcgttattg ga                                      22

<210> SEQ ID NO 27
<211> LENGTH: 22
<212> TYPE: DNA
<213> ORGANISM: Artificial Sequence
<220> FEATURE:
<223> OTHER INFORMATION: hsp70-8 primer

<400> SEQUENCE: 27
aaataccgct gccatcccac cg                                      22
```

```
<210> SEQ ID NO 28
<211> LENGTH: 4
<212> TYPE: PRT
<213> ORGANISM: Artificial Sequence
<220> FEATURE:
<223> OTHER INFORMATION: conserved tetrapeptide signature S cerevisiae,
      amino acids 39-42

<400> SEQUENCE: 28

His Val Thr Val
1

<210> SEQ ID NO 29
<211> LENGTH: 4
<212> TYPE: PRT
<213> ORGANISM: Artificial Sequence
<220> FEATURE:
<223> OTHER INFORMATION: conserved tetrapeptide signature A thaliana-
      amino acids 43-46

<400> SEQUENCE: 29

His Val Thr Val
1

<210> SEQ ID NO 30
<211> LENGTH: 4
<212> TYPE: PRT
<213> ORGANISM: Artificial Sequence
<220> FEATURE:
<223> OTHER INFORMATION: conserved tetrapeptide signature humain, amino
      acids 252-255

<400> SEQUENCE: 30

His Cys Thr Thr
1

<210> SEQ ID NO 31
<211> LENGTH: 4
<212> TYPE: PRT
<213> ORGANISM: Artificial Sequence
<220> FEATURE:
<223> OTHER INFORMATION: mutated motif to alanine in mH2A1.1, amino
      acids 213 - 216

<400> SEQUENCE: 31

Ala Ala Ala Ala
1

<210> SEQ ID NO 32
<211> LENGTH: 4
<212> TYPE: PRT
<213> ORGANISM: Artificial Sequence
<220> FEATURE:
<223> OTHER INFORMATION: S cerevisiae, amino acids 150-153

<400> SEQUENCE: 32

His Val Ser Leu
1

<210> SEQ ID NO 33
<211> LENGTH: 4
<212> TYPE: PRT
<213> ORGANISM: Artificial Sequence
<220> FEATURE:
<223> OTHER INFORMATION: A thaliana- amino acids 119-122
```

```
<400> SEQUENCE: 33

His Leu Ser Leu
1

<210> SEQ ID NO 34
<211> LENGTH: 4
<212> TYPE: PRT
<213> ORGANISM: Artificial Sequence
<220> FEATURE:
<223> OTHER INFORMATION: signature humain, amino acids 331-334

<400> SEQUENCE: 34

His Ile Thr Leu
1

<210> SEQ ID NO 35
<211> LENGTH: 4
<212> TYPE: PRT
<213> ORGANISM: Artificial Sequence
<220> FEATURE:
<223> OTHER INFORMATION: mH2A1.1 amino acids 273-276

<400> SEQUENCE: 35

His Cys Asn Ser
1
```

PARP INHIBITORS

CROSS-REFERENCE TO RELATED APPLICATIONS

This application is a 371 U.S. National Stage of International Application No. PCT/IB2006/003224, filed Nov. 14, 2006 and published in English as WO 2007/054814 A1 on May 17, 2007, which claims the benefit of U.S. Provisional Application No. 60/736,588, filed Nov. 14, 2005. The disclosures of the above applications are expressly incorporated herein by reference.

FIELD OF THE INVENTION

The present invention relates to new inhibitors of the nucleic enzyme poly(adenosine 5'-diphospho-ribose) polymerase ["poly(ADP-ribose) polymerase" or "PARP", which is also sometimes called "PARS" for poly(ADP-ribose) synthetase]. More particularly, the invention relates to the use of PARP inhibitors to prevent and/or treat tissue damage resulting from cell damage or death due to necrosis or apoptosis; neural tissue damage resulting from ischemia and reperfusion injury; neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells.

BACKGROUND

Poly(ADP-ribose) polymerase ("PARP") is an enzyme located in the nuclei of cells of various organs, including muscle, heart and brain cells. PARP plays a physiological role in the repair of strand breaks in DNA. Once activated by damaged DNA fragments, e.g., after exposure to chemotherapy, ionizing radiation, oxygen free radicals, or nitric oxide (NO), PARP catalyzes the transfer of ADP-ribose units from nicotinamide adenine dinucleotide (NAD$^+$) to nuclear acceptor proteins, and is responsible for the formation of protein-bound linear and branched homo-ADP-ribose polymers. The PARP's activation results in the attachment of up to 100 ADP-ribose units to a variety of nuclear proteins, including histones, topoisomerases, DNA and RNA polymerases, DNA ligases, $Ca^{2+}$- and $Mg^{2+}$-dependent endonucleases and PARP itself. While the exact range of functions of PARP has not been fully established, this enzyme is thought to play a role in enhancing DNA repair and maintaining DNA integrity.

During major cellular stresses, however, the extensive activation of PARP can rapidly lead to cell damage or death through depletion of energy stores. Four molecules of ATP are consumed for every molecule of NAD (the source of ADP-ribose) regenerated. Thus, NAD, the substrate of PARP, is depleted by massive PARP activation and, in the efforts to re-synthesize NAD, ATP may also be depleted.

It has been reported that PARP activation plays a key role in both NMDA- and NO-induced neurotoxicity, as shown by the use of PARP inhibitors to prevent such toxicity in cortical cultures in proportion to their potencies as inhibitors of this enzyme (ZHANG et al., *Science*, vol. 263, p: 687-89, 1994); and in hippocampal slices (WALLIS et al., *NeuroReport*, vol. 5(3), p: 245-48, 1993). The potential role of PARP inhibitors in treating neurodegenerative diseases and head trauma has thus been known. Research, however, continues to pinpoint the exact mechanisms of their salutary effect in cerebral ischemia, (ENDRES et al., *J. Cereb. Blood Flow Metabol.*, vol. 17, p: 1143-51, 1997) and in traumatic brain injury (WALLIS et al., *Brain Res.*, vol. 710, p: 169-77, 1996).

The PARP inhibitors are additionally useful for treating cardiovascular diseases. Ischemia, a deficiency of oxygen and glucose in a part of the body, can be caused by an obstruction in the blood vessel supplying that area or a massive hemorrhage. Two severe forms, heart attack and stroke, are major killers in the developed world. Cell death results directly and also occurs when the deprived area is reperfused. It has been demonstrated that single injections of PARP inhibitors have reduced the infarct size caused by ischemia and reperfusion of the heart or skeletal muscle in rabbits. In these studies, a single injection of the PARP inhibitor, 3-amino-benzamide (10 mg/kg), either one minute before occlusion or one minute before reperfusion, caused similar reductions in infarct size in the heart (32-42%). Another PARP inhibitor, 1,5-dihydroxy-isoquinoline (1 mg/kg), reduced infarct size by a comparable degree (38-48%; THIEMERMANN et al., *Proc. Natl. Acad. Sci. USA*, vol. 94, p: 679-83, 1997). This finding has suggested that PARP inhibitors might be able to salvage previously ischemic heart or skeletal muscle tissue. Presently, PARP inhibitors are being developed to treat ischemia/reperfusion injuries (ZHANG, The Prospect for Improved Medicines, Ashley Publications Ltd, 1999).

PARP activation has also been shown to provide an index of damage following neurotoxic insults by glutamate (via NMDA receptor stimulation), reactive oxygen intermediates, amyloid .beta.-protein, n-methyl-4-phenyl-1,2,3,6-tetrahydropyridine (MPTP) and its active metabolite N-methyl-4-phenylpyridine (MPP$^+$), which participate in pathological conditions such as stroke, Alzheimer's disease and Parkinson's disease (ZHANG et al., *J. Neurochem.*, vol. 65(3), p: 1411-14, 1995). Other studies have continued to explore the role of PARP activation in cerebellar granule cells in vitro and in MPTP neurotoxicity (COSI et al., *Ann. N. Y. Acad. Sci.*, vol. 825, p: 366-79, 1997; COSI et al., *Brain Res.*, vol. 729, p: 264-69, 1996).

Neural damage following stroke and other neurodegenerative processes is thought to result from a massive release of the excitatory neurotransmitter glutamate, which acts upon the N-methyl-D-aspartate (NMDA) receptors and other subtype receptors. Glutamate serves as the predominate excitatory neurotransmitter in the central nervous system (CNS). Neurons release glutamate in great quantities when they are deprived of oxygen, as may occur during an ischemic brain insult such as a stroke or heart attack. This excess release of glutamate in turn causes over-stimulation (excitotoxicity) of N-methyl-D-aspartate (NMDA), AMPA, Kainate and MGR receptors. When glutamate binds to these receptors, ion channels in the receptors open, permitting flows of ions across their cell membranes, e.g., $Ca^{2+}$ and $Na^+$ into the cells and $K^+$ out of the cells. These flows of ions, especially the influx of $Ca^{2+}$, cause overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult. Recent studies have also advanced a glutamatergic basis for compulsive disorders, particularly drug dependence. Evidence includes findings in many animal species, as well as, in cerebral cortical cultures treated with glutamate or NMDA, that glutamate receptor antagonists block neural damage following vascular stroke (DAWSON et al., *H. Hunt Batjer ed.*, p: 319-25, 1997). Attempts to prevent excitotoxicity by blocking NMDA, AMPA, Kainate and MGR receptors have proven difficult because each receptor has multiple sites to which glutamate may bind. Many of the compositions that are effective in blocking the receptors are also toxic to animals. As such, there is no known effective treatment for glutamate abnormalities.

The stimulation of NMDA receptors, in turn, activates the enzyme neuronal nitric oxide synthase (NNOS), which causes the formation of nitric oxide (NO), which more directly mediates neurotoxicity. Protection against NMDA neurotoxicity has occurred following treatment with NOS inhibitors (DAWSON et al., *Proc. Natl. Acad. Sci. USA*, vol. 88, p: 6368-71, 1991; DAWSON et al., *J. Neurosci.*, vol. 13(6), p: 2651-61, 1993). Protection against NMDA neurotoxicity can also occur in cortical cultures from mice with targeted disruption of NNOS (DAWSON et al., *J. Neurosci.*, vol. 16(8), p: 2479-87, 1996).

It is known that neural damage following vascular stroke is markedly diminished in animals treated with NOS inhibitors or in mice with NNOS gene disruption (IADECOLA, *Trends Neurosci.*, vol. 20(3), p: 132-39, 1997; HUANG et al., *Science*, vol. 265, p: 1883-85, 1994; BECKMAN et al., *Biochem. Soc. Trans.*, vol. 21, p: 330-34, 1993). Either NO or peroxynitrite can cause DNA damage, which activates PARP. Further support for this is provided in SZABO et al. (*Proc. Natl. Acad. Sci. USA*, vol. 93, p: 1753-58, 1996).

It is also known that PARP inhibitors affect DNA repair generally. CRISTOVAO et al. (*Terato., Carcino., and Muta.*, vol. 16, p: 219-27, 1996) discusses the effect of hydrogen peroxide and .gamma.-radiation on DNA strand breaks in the presence of and in the absence of 3-aminobenzamide, a potent inhibitor of PARP. CRISTOVAO et al. observed a PARP-dependent recovery of DNA strand breaks in leukocytes treated with hydrogen peroxide.

Evidence also exists that PARP inhibitors are useful for treating inflammatory conditions such as inflammatory bowel disorders (SOUTHAN et al., *Br. J. Pharm.*, vol. 117, p: 619-32, 1996; SZABO et al., *J. Biol. Chem.*, vol. 272, p: 9030-36, 1997) or arthritis (SZABO et al., *Portland Press Proc.*, vol. 15, p: 280-281, 1998; SZABO, *Eur. J. Biochem.*, vol. 350(1), p: 1-19, 1998; SZABO et al., *Proc. Natl. Acad. Sci. USA*, vol. 95(7), p: 3667-72, 1998; SZABO et al., *Proc. Natl. Acad. Sci. USA*, vol. 93, p: 1753-58, 1996; BAUER et al., *Intl. J. Oncol.*, vol. 8, p: 239-52, 1996; HUGHES et al., *J. Immuno.*, vol. 153, p: 3319-25, 1994). Thus, SALZMAN et al. (*Japanese J. Pharm.*, vol. 75 (Supp. I), p: 15, 1997) shows that 3-aminobenzamide, a specific inhibitor of PARP activity, reduced the inflammatory response and restored the morphology and the energetic status of the distal colon in rats suffering from colitis induced by intraluminal administration of the hapten trinitrobenzene sulfonic acid in 50% ethanol. As another example, SZABO et al. (*Japanese J. Pharm.*, vol. 75 (Supp. I), p: 102, 1997) discusses the ability of PARP inhibitors to prevent or treat collagen-induced arthritis.

Further, PARP inhibitors appear to be useful for treating diabetes and have been studied at the clinical level to prevent development of insulin-dependent diabetes mellitus in susceptible individuals (SALDEEN et al., *Mol. Cellular Endocrinol.*, vol. 139, p: 99-107, 1998). In models of Type I diabetes induced by toxins such as streptozocin and alloxan that destroy pancreatic islet cells, it has been shown that knock-out mice lacking PARP are resistant to cell destruction and diabetes development (PIEPER et al., *Trends Pharmacolog. Sci.*, vol. 20, p: 171-181, 1999; BURKART et al., *Nature Medicine*, vol. 5, p: 314-319, 1999). Administration of nicotinamide, a weak PARP inhibitor and a free-radical scavenger, prevents development of diabetes in a spontaneous autoimmune diabetes model, the non-obese, diabetic mouse (PIEPER et al., 1999, aforementioned). Hence, potent and specific PARP inhibitors may be useful as diabetes-prevention therapeutics.

Further still, PARP inhibitors have been shown to be useful for treating endotoxic shock or septic shock (ZINGARELLI et al., *Shock*, vol. 5, p: 258-64, 1996; CUZZOCREA, *Brit. J. Pharm.*, vol. 122, p: 493-503, 1997). ZINGARELLI et al. suggests that inhibition of the DNA repair cycle triggered by poly(ADP ribose) synthetase has protective effects against vascular failure in endotoxic shock. ZINGARELLI et al. found that nicotinamide protects against delayed, NO-mediated vascular failure in endotoxic shock. ZINGARELLI et al. also found that the actions of nicotinamide may be related to inhibition of the NO-mediated activation of the energy-consuming DNA repair cycle, triggered by poly(ADP ribose) synthetase.

Yet another known use for PARP inhibitors is treating cancer. In fact, the PARP's activity can contribute to the resistance that often develops to various types of cancer therapies, because this cellular ADP-ribose transfer process is associated with the repair of DNA strand breakage in response to DNA damage caused by radiotherapy or chemotherapy. Consequently, inhibition of PARP may retard intracellular DNA repair and enhance the antitumor effects of cancer therapy. Indeed, in vitro and in vivo data show that many PARP inhibitors potentiate the effects of ionizing radiation (U.S. Pat. Nos. 5,032,617; 5,215,738; 5,041,653; 5,177,075) or cytotoxic drugs such as alkylating agents (WELTIN et al., *Oncol. Res.*, vol. 6(9), p: 399-403, 1994). Thus, inhibitors of the PARP enzyme are useful as adjunct cancer chemotherapeutics.

Still another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs (MAO et al., *Pain*, vol. 72, p: 355-366, 1997).

PARP inhibitors have also been used to extend the lifespan and proliferative capacity of cells including treatment of diseases such as skin aging (U.S. Pat. No. 5,589,483), Alzheimer's disease, atherosclerosis, osteoarthritis, osteoporosis, muscular dystrophy, degenerative diseases of skeletal muscle involving replicative senescence, age-related macular degeneration, immune senescence, AIDS, and other immune senescence diseases; and to alter gene expression of senescent cells.

Large numbers of PARP inhibitors have been described. For example, BANASIK et al. (*J. Biol. Chem.*, vol. 267(3), p: 1569-75, 1992) examined the PARP-inhibiting activity of over one hundred compounds, the most potent of which were 4-amino-1,8-naphthalimide, 6(5H)-phenanthridone, 2-nitro-6(5H)-phenanthridone, and 1,5-dihydroxyisoquinoline. GRIFFIN et al. reported the PARP-inhibiting activity for certain benzamide compounds (*Anti-Cancer Drug Design*, vol. 10, p: 507-514, 1995; U.S. Pat. No. 5,756,510), benzimidazole compounds (WO 97/04771), and quinalozinone compounds (WO 98/33802). SUTO et al. reported PARP inhibition by certain dihydroisoquinoline compounds (*Anti-Cancer Drug Design*, vol. 7, p: 107-117, 1991). GRIFFIN et al. have reported other PARP inhibitors of the quinazoline class (*J. Med. Chem.*, vol. 41, p: 5247-5256, 1998). Finally, WO 99/11622, WO 99/11623, WO 99/11624, WO 99/11628, WO 99/11644, WO 99/11645, and WO 99/11649 also describe various PARP-inhibiting compounds.

However, the approach of using these PARP inhibitors in the ways discussed above has been limited in effect. For example, side effects have been observed with some of the best-known PARP inhibitors (MILAM et al., *Science*, vol. 223, p: 589-91, 1984). Specifically, the PARP inhibitors 3-aminobenzamide and benzamide not only inhibited the action of PARP but also were shown to affect cell viability, glucose metabolism, and DNA synthesis. Thus, it was concluded that the usefulness of these PARP inhibitors may be severely restricted by the difficulty of finding a dose that will inhibit the enzyme without producing additional metabolic effects.

Accordingly, there remains a need for compounds that inhibit more specifically PARP activity, compositions containing those compounds, and methods utilizing those compounds, wherein the compounds produce more potent and reliable effects with fewer side effects, with respect to inhibiting PARP activity and treating the diseases and conditions discussed herein.

Macro-H2A1 and macroH2A2 histones are particularly enigmatic histone variants having an N-terminal region with high sequence homology to H2A, and also containing an extensive non histone C-terminal tail that comprises nearly two third of the protein (25 kDa). The human genome contains two genes that code for macroH2A histones. The MACROH2A1 gene encodes two subtypes MACROH2A1.1 and MACROH2A1.2 produced by alternative splicing. A second gene codes for MACROH2A2 (CHADWICK and WILLARD, *Human. Mol. Genet.*, vol. 10, p: 1101-1113, 2001). These proteins appear to be enriched in heterochromatin such as the inactive X chromosome (Xi) in female mammals (COSTANZI and PEHRSON, *Nature*, vol. 393, p: 599-601, 1998), and discrete heterochromatic loci in senescent and quiescent cells (ZHANG et al., *Dev. Cell*, vol. 8, p: 19-30, 2005; GRIGORYEV et al., *J. Cell. Sci.*, vol. 117, p: 6153-6162, 2004). MacroH2A is highly localized in female cells as a distinct nuclear body, referred to as a macro chromatin body (MCB), which is coincident with the Xi and the Barr body (COSTANZI and PEHRSON, aforementioned, 1998). The C-terminal region of macroH2A contains a domain termed "macro domain", which is found alone or in multiple copies in a number of otherwise unrelated proteins (PEHRSON and FUJI, *Nuc. Acids Res.*, vol. 26, p: 2837-2849, 1998), and which is critical for macroH2A MCB formation (CHADWICK et al., *Nuc. Acids Res.*, vol. 29(13), p: 2699-2705, 2001). It has been suggested that this macro domain defines a superfamily of phosphoesterases that act on ADP ribose derivatives (ALLEN et al., *J. Mol. Biol.*, vol. 330, p: 503-511, 2003). Recently, KUSTATSCHER et al. (*Nat. Struct. Mol. Biol.*, vol. 12(7), p: 624-5, 2005) shows that macroH2A1.1 binds to monomeric ADP-ribose and to O-acetyl-ADP-ribose (a NAD metabolite). The authors identify Phe348, Asp203, Gly224 and Gly314 as critical residues for O-acetyl-ADP-ribose binding. Nevertheless, the specific macroH2A function is still unknown.

SUMMARY OF THE INVENTION

The inhibitor of the nucleic enzyme poly(adenosine 5'-diphospho-ribose) polymerase ["poly(ADP-ribose) polymerase (PARP) of the invention have a phosphoesterase activity, and comprises an amino acid sequence, which is derived from the C-terminal non-histone domain of a macroH2A histone, optionally fused and/or coupled to at least one heterologous sequence.

As used therein, a "phosphoesterase activity" means the catalysis of the hydrolysis of one of the two ester bonds in a phosphodiester compound.

In another embodiment, the composition of the invention comprises (i) an inhibitor of the nucleic enzyme poly(adenosine 5'-diphospho-ribose) polymerase ["poly(ADP-ribose) polymerase (PARP) having a phosphoesterase activity, and comprising an amino acid sequence, which is derived from the C-terminal non-histone domain of a macroH2A histone, optionally fused and/or coupled to at least one heterologous sequence, a nucleic acid coding thereof, or a vector comprising said nucleic acid, and (ii) a pharmaceutically acceptable vehicle.

In an additional embodiment, a method of prophylactic or therapeutic treatment of a subject suffering from a disease associated with PARP activation comprising the step of administrating an effective amount of a composition comprising (i) an inhibitor of the nucleic enzyme poly(adenosine 5'-diphospho-ribose) polymerase ["poly(ADP-ribose) polymerase (PARP) having a phosphoesterase activity, and comprising an amino acid sequence, which is derived from the C-terminal non-histone domain of a macroH2A histone, optionally fused and/or coupled to at least one heterologous sequence, a nucleic acid coding thereof, or a vector comprising said nucleic acid, and (ii) a pharmaceutically acceptable vehicle to said subject.

BRIEF DESCRIPTION OF THE DRAWINGS

FIG. 11 shows the sequence alignment of macroH2A1.1 (NP_613075, SEQ ID NO: 18) macroH2A1.2 (NP_004884, SEQ ID NO: 19) and macroH2A2 (NP_061119, SEQ ID NO: 20) macro domains with some selected macro domains of non-histone proteins. Residues conserved in the macro domain are marked in red. The residues altered by the alternative splicing of the MacroH2A1 gene are underlined. This altered region is predicted to bind phosphate groups and to hydrolyze the ADP-ribose (G, D, I, T consensus motif). AF1521, SEQ ID NO: 21 is a protein from *Archaeoglobus fulgidus* with homology to the macro domain of MacroH2A. AF1521 is crystallized. NP_598908.1, SEQ ID NO: 22 is an AF 1521 orthologue from mouse. YBR022WP is a *S. cerevisiae* protein with exclusively a macro domain. YBR022WP, SEQ ID NO: 23 was reported to processes the 1"-phosphat group of 1"-phospho-ADP-ribose.

FIG. 16 shows the sequence alignment of macroH2A with known phosphoesterases. The two conserved tetrapeptide signatures in *S. cerivisiae* (P53314, SEQ ID NO: 28 and SEQ ID NO: 32, first row), *A. thaliana* (Y1 1650, SEQ ID NO: 29 and SEQ ID NO: 33, second row) and human (BC006392.1, SEQ ID NO: 30 and SEQ ID NO: 34, third row) phosphoesterases are shown and aligned with human mH2A1.1, SEQ ID NO: 1 (fourth row), human mH2A1.2, SEQ ID NO: 2 (fifth row) and human mH2A2, SEQ ID NO: 3 (sixth row). These alignments highlight the importance of the H, X, T, X consensus motif (eighth row) located in the active site. This motif was mutated to alanine (A, A, A, A) in mH2A1.1 (mH2A1.1-mut, SEQ ID NO: 31 and SEQ ID NO: 35, seventh row).

DETAILED DESCRIPTION

Figure 1:
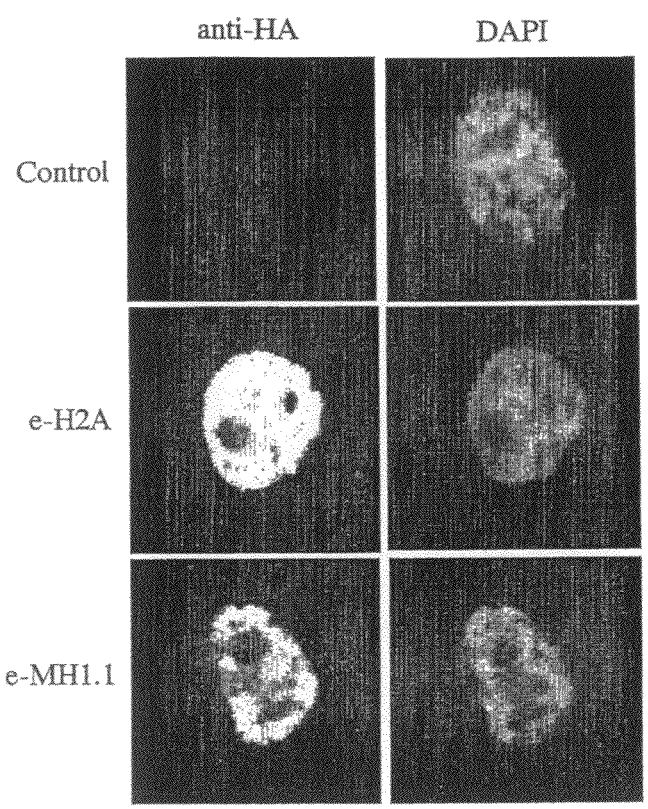
FIG. 1 shows the immunofluorescence staining obtained with anti-HA antibody (anti-HA) on Hela cells stably expressing tagged macro-H2A1.1 (e-MH1.1) and H2A (e-H2A) histones, or not (control) compared to the chromatin localization (DAPI).

The inventors have now discovered that macroH2A histone can specifically bind PARP-1 through its C-terminal non-histone domain, and consequently repress the PARP-1 activity through the phopshoesterase activity of its macro domain.

This invention provides a new tool to inhibit the nucleic enzyme poly(adenosine 5'-diphospho-ribose) polymerase ["poly(ADP-ribose) polymerase" (PARP) and methods to treat and/or prevent PARP activation associated diseases.

Consequently, in one aspect the present invention relates to an inhibitor of the nucleic enzyme poly(adenosine 5'-diphospho-ribose) polymerase ["poly(ADP-ribose) polymerase" having a phosphoesterase activity, and comprising an amino acid sequence, which is derived from the C-terminal non-histone domain of a macroH2A histone, optionally fused and/or coupled to at least one heterologous sequence.

Advantageously, said inhibitor is a synthetic or a recombinant polypeptide.

As used herein the term "macroH2A histone" relates to an unusual histone H2A variant that have a large C-terminal non-histone domain (for a review, see PERCHE et al., Med. Sci., vol. 19(11), p: 1137-45, 2003). Actually, three human macroH2A histones, having such C-terminal non-histone domain, have been identified: macroH2A1.1 and macroH2A1.2 produced by alternative splicing from a single gene, and macroH2A2.

As used herein the term "C-terminal non-histone domain" relates to the large C-terminal region of macroH2A histone that shares no homology with histone H2A. Said non-histone domain can be identified from one of skills in the art with simple sequence analysis. As an example, said non-histone domain corresponds to residues 121 to 369 of human macroH2A1.1 (SEQ ID NO:1), residues 121 to 371 of human macroH2A1.2 (SEQ ID NO: 2), and residues 121 to 372 of human macroH2A2 (SEQ ID NO: 3).

Advantageously, the C-terminal non-histone domain of macroH2A histone is selected in the group comprising the C-terminal non-histone domain of macroH2A1.1, macroH2A1.2, and macroH2A2 histones, preferably the C-terminal non-histone domain of human macroH2A1.1, macroH2A1.2, and macroH2A2 histones. Preferably, said C-terminal non-histone domain corresponds to the C-terminal non-histone domain of macroH2A1.1.

As used herein an "heterologous sequence" relates to any amino acid sequence which is not derived from macroH2A histone variants, like macroH2A1.1, macroH2A1.2, and macroH2A2. This heterologous sequence can for example consist of an amino acids sequence, which facilitates penetration of the inhibitor of the invention from the outside medium into the intracellular medium, and quite specifically into the nucleus of the cell. Such amino acids sequence are well known from one of skill in the art, and examples of such amino acids sequence are described in EP 1512696, WO 02/10201, EP 15226183, and WO 2004/069279. This heterologous sequence can also for example facilitate the purification of the inhibitor from bacteria. Such amino acids sequence are also well known from one of skill in the art, and examples of such amino acids sequence include His tag, GST protein, FLAG tag, and HA tag.

An amino acid sequence "derived from" or a "derivative of" the C-terminal non-histone domain of macroH2A histone selected in the group comprising the C-terminal non-histone domain of human macroH2A1.1 (amino acid 121 to 367 of SEQ ID NO:1), of human macroH2A1.2 (amino acids 121 to 371 of SEQ ID NO:2), and of human macroH2A2 (amino acids 121 to 372 of SEQ ID NO:3) relates to amino acid sequence sharing an identity of more than 60% with said C-terminal non-histone domain or fragments thereof, for example of more than 70% or of more than 80%, preferably of more than 85%, most preferably of more than 90% and advantageously of more than 95%.

The identity differences between the above described C-terminal non-histone domains and the amino acid sequence of the inhibitor of the invention result from amino acids substitution in the amino acid sequence of said inhibitor.

Preferably, the substituted amino acid(s) in these C-terminal non-histone domains domains preserve or increase the phosphoesterase activity of said domains Such substitutions can be identified by one of skills in the art in view of its general knowledge and/or with simple experiments. Preferably, said substitutions correspond to amino acid residues having the same charge, hydrophopathy, sterical hindrance, and/or chemical function as related to the corresponding residues in the C-terminal non-histone domains of macroH2A histones.

According to a specific embodiment, said amino acid sequence have an identity of 100% with said macroH2A C-terminal non-histone domain or fragments thereof.

Advantageously, said amino acid sequence which is derived from the non-histone domain of a macroH2A histone is less than 350 amino acids in length, preferably less than 300 amino acids, as an example less than 250 amino acids or less than 200 amino acids in length, and more preferably less than 150 amino acids.

According to a preferred embodiment, said amino acid sequence which is derived from the non-histone domain of a macroH2A histone does not comprise the macroH2A histone fold domain having homology with histone H2A (LUGER et al., Nature, vol. 389 (6648), p: 251-260, 1997), herein incorporated by reference), and preferably said amino acid sequence does not comprise any sequence having homology with histone H2A.

Advantageously, said amino acid sequence does not comprise any histone fold domain.

Advantageously, said amino acid sequence which is derived from the non-histone domain of a macroH2A histone is more than 20 amino acids in length, preferably more than 25 amino acids, as an example more than 35 amino acids or more than 50 amino acids in length, and more preferably more than 60 amino acids.

According to a preferred embodiment, said amino acid sequence, which is derived from the non-histone domain of a macroH2A histone comprises the macro domain of a macroH2A histone.

As used herein the term "macro domain" relates to a region present in the C-terminal non-histone domain of macroH2A histones, and which is also found alone or in multiple copies in a number of otherwise unrelated proteins (PEHRSON and FUJI, 1998, aforementioned; ALLEN et al., 2003, aforementioned). Said macro domain can be also simply identified from one of skills in the art with simple sequence analysis. As an example, said macro domain corresponds to residues 184 to 369, preferably 202 to 369 of human macroH2A1.1 (SEQ ID NO:1), residues 183 to 371, preferably 201 to 371 of human macroH2A1.2 (SEQ ID NO:2), and residues 184 to 372, preferably 202 to 372 of human macroH2A2 (SEQ ID NO:3). Said macro domain includes critical residues for phosphoesterase activity, some of which are identified in the examples below, and in KUSTATSCHER et al. (2005, abovementioned, herein incorporated by reference). Some potentially critical residues for phosphoestrase activity can also be identified as the conserved residues in macro domains of AF1521 family members described in ALLEN et al. (2003, abovementioned, herein incorporated by reference). Finally, said macro domain of macroH2A histone is potentially an ADP binding domain as described in KARRAS et al. (*EMBO journal*, vol. 24(11), p: 1911-1920, 2005: See FIGS. 6A and B).

In a second aspect the invention relates to a nucleic acid encoding for an inhibitor as described above.

Said nucleic acid corresponds to RNA or DNA, preferably to DNA.

According to a particular embodiment, the nucleic acid encoding the inhibitor is operatively linked to a gene expression sequence, which directs the expression of nucleic acid within a prokarotic or an eukaryotic cell, preferably an eukaryotic cell. The "gene expression sequence" is any regulatory nucleotide sequence, such as a promoter sequence or promoter-enhancer combination, which facilitates the efficient transcription and translation of the inhibitor to which it is operatively linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, beta.-actin promoter, muscle creatine kinase promoter, human elongation factor promoter and other constitutive promoters. Exemplary viral promoters which function constitutively in eukaryotic cells include, for example, promoters from the simian virus (e.g., SV40), papilloma virus, adenovirus, human immunodeficiency virus (HIV), cytomegalovirus (CMV), Rous sarcoma virus (RSV), hepatitis B virus (HBV), the long terminal repeats (LTR) of Moloney leukemia virus and other retroviruses, and the thymidine kinase promoter of herpes simplex virus. Others constitutive promoters are known to those of ordinary skill in the art. The promoters useful as gene expression sequences of the invention also include inducible promoters, such as promoters inducible under stress conditions. Inducible promoters are expressed in the presence of an inducing agent. For example, the hsp70-1 promoter is induced to promote transcription and translation, after a heat shock. Others inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired. Preferably, the gene expression sequence include a nuclear localization signal (NLS) fused to the nucleic acid sequence coding for the inhibitor of the invention in order to facilitate translocation of said inhibitor into the nucleus of the cell. NLS sequences are well known from one of skills in the art.

As used herein, the inhibitor nucleic acid sequence and the gene expression sequence are said to be "operably linked" when they are covalently linked in such a way as to place the expression or transcription and/or translation of the inhibitor coding sequence under the influence or control of the gene expression sequence. Two DNA sequences are said to be operably linked if induction of a promoter in the 5' gene expression sequence results in the transcription of the inhibitor sequence and if the nature of the linkage between the two DNA sequences does not (1) result in the introduction of a frame-shift mutation, (2) interfere with the ability of the promoter region to direct the transcription of the inhibitor sequence, or (3) interfere with the ability of the corresponding RNA transcript to be translated into a protein. Thus, a gene expression sequence would be operably linked to a inhibitor nucleic acid sequence if the gene expression sequence were capable of effecting transcription of that nucleic acid sequence such that the resulting transcript is translated into the desired protein or polypeptide.

The inhibitor nucleic acid may be delivered in vivo alone or in association with a vector.

In a third aspect the invention relates to a vector comprising a nucleic acid sequence as previously described.

In its broadest sense, a "vector" is any vehicle capable of facilitating the transfer of the inhibitor nucleic acid to the cells and preferably cells expressing nucleic enzyme poly(adenosine 5'-diphospho-ribose) polymerase ["poly(ADP-ribose) polymerase" (PARP). Preferably, the vector transports the nucleic acid to cells with reduced degradation relative to the extent of degradation that would result in the absence of the vector. The vector optionally includes the above-described gene expression sequence to enhance expression of the inhibitor nucleic acid in PARP expressing cells. In general, the vectors useful in the invention include, but are not limited to, plasmids, phagemids, viruses, other vehicles derived from viral or bacterial sources that have been manipulated by the insertion or incorporation of the inhibitor nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffion, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

The nucleic acid vector can include selectable markers that are active both in bacteria and in mammalian cells.

According to a preferred embodiment, the nucleic acid vector of the present invention corresponds to "naked DNA" like plasmids, cosmids or phagemids. Such naked DNA can be associated with non-lipid cationic polymers (WU and WU, J. Biol. Chem., vol. 263, p: 14621-4, 1988) or liposomes (BRIGHMAN et al., Am. J. Med. Sci., vol. 298, p: 278-81, 1989) to form complexes enhancing cellular uptake.

According to another preferred embodiment, the nucleic acid vector is a viral vector adapted for in vivo gene therapy protocols. Examples of appropriate viral vectors includes retroviral vectors as described in EP 0871459, EP 0386882 and EP 1222300 and adenovirus vectors as described in US 2004/265273 and U.S. Pat. No. 6,638,502. In this case, the internalization of virus occurs through the specific interaction of the viral envelope with a cell surface receptor, followed by receptor-mediated endocytosis of the virus/receptor complex.

According to a fourth aspect the present invention relates to a composition, preferably a pharmaceutical composition, comprising (i) an inhibitor as described previously, a nucleic acid coding thereof, or a vector comprising said nucleic acid, and (ii) a pharmaceutically acceptable vehicle.

The composition of the invention inhibits PARP activity, and can be used to prevent and/or to treat diseases associated with PARP activation. For example, the composition of the invention can be used to treat or prevent neural tissue damage resulting from cell damage or death due to necrosis or apoptosis, like cardiovascular tissue damage resulting from cardiac ischemia or reperfusion injury or neurodegenerative diseases. The composition of the invention can be used to extend or increase the lifespan or proliferation of cells and thus to treat or prevent diseases associated therewith and induced or exacerbated by cellular senescence including skin aging, atherosclerosis, osteoarthritis, osteoporosis, muscular dystrophy, degenerative diseases of skeletal muscle involving replicative senescence, age-related macular degeneration, immune senescence, AIDS and other immune senescence diseases, and other diseases associated with cellular senescence and aging, as well as to alter the gene expression of senescent cells. The composition of the invention can further be used to treat cancer and to radiosensitize hypoxic tumor cells to render the tumor cells more susceptible to radiation therapy and to prevent the tumor cells from recovering from potentially lethal damage of DNA after radiation therapy, presumably by their ability to prevent DNA repair.

Pharmaceutically acceptable vehicles are well known from one of skills in the art. As an example of pharmaceutically acceptable vehicle, the composition may comprise emulsions, microemulsions, oil-in-water emulsions, anhydrous lipids and oil-in-water emulsions, other types of emulsions. The composition may also comprise one or more additives (e.g., diluents, excipients, stabilizers, preservatives). See, generally, *Ullmann's Encyclopedia of Industrial Chemistry*, 6$^{th}$ Ed. (various editors, 1989-1998, Marcel Dekker); and *Pharmaceutical Dosage Forms and Drug Delivery Systems* (ANSEL et al., 1994, WILLIAMS & WILKINS).

Inhibitor of the invention, nucleic acids encoding thereof or nucleic acid vectors comprising such nucleic acid may be solubilized in a buffer or water or incorporated in emulsions and microemulsions. Suitable buffers include, but are not limited to, phosphate buffered saline $Ca^{++}/Mg^{++}$ free (PBS), phosphate buffered saline (PBS), normal saline (150 mM NaCl in water), Tris buffer and surfactants.

There are numerous causes of peptide instability or degradation, including hydrolysis and denaturation. Hydrophobic interaction may cause clumping of molecules together (i.e. aggregation). This result may entail diminution of the PARP repression. Stabilizers may be added to lessen or prevent such problems.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from ionic and non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (e.g., glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycrol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

Advantageously, said composition comprises the inhibitor of the invention, a nucleic acid coding thereof, or a nucleic acid vector in an amount sufficient to inhibit PARP activity.

As an example, said composition can comprise a concentration of said inhibitor of more than $10^{-12}$ M, preferably more than $10^{-9}$ M, as an example more than $10^{-8}$ M or more than $10^{-6}$ M, and most preferably more than $10^{-3}$ M.

In a fifth aspect the present invention relates to a method of prophylactic or therapeutic treatment of a subject suffering from a disease associated with PARP activation comprising the step of administrating an effective amount of a composition as described above to said subject.

As used herein, the term "subject" denotes a Mammal, such as a rodent, a feline, a canine and a primate. The subject is an animal such as cow, pig, horse, chicken, cat, dog and most preferably a human.

The inhibitors of the invention inhibit PARP activity and, thus, are believed to be useful for treating tissue damage resulting from cell damage or death due to necrosis or apoptosis, neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory disorders like inflammatory bowel disorders such as colitis and Crohn's disease, muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize tumor cells.

Examples of neurodegenerative diseases that are treatable by the method of the present invention include, without limitation, trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barre syndrome; Alzheimer's disease; Huntington's Disease and Parkinson's disease.

Examples of cardiovascular disorders that can either cause ischemia or are caused by reperfusion of the heart include, but are not limited to, coronary artery disease, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, tissue damage related to PARP activation.

For example, the methods of the invention are useful for treating cancers and radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor. Examples of additional therapeutic agents that may be used in conjunction with the inhibitor of the invention include, but are not limited to: 5-fluorouracil, leucovorin, 5'-amino-5' deoxythymidine, oxygen, carbogen, red cell transfusions, perfluorocarbon (e.g., Fluosol-DA), 2,3-DPG, BW12C, calcium channel blockers, pentoxyfylline, antiangiogenesis compounds, hydralazine, L-BSO, adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

For medical use, the amount required of the inhibitor of the invention to achieve a therapeutic effect will vary according to the particular inhibitor administered, the route of administration, the mammal under treatment, and the particular disorder or disease concerned. A suitable systemic dose of the inhibitor of the invention for a mammal suffering from, or likely to suffer from, any condition as described herein is typically in the range of about 0.001 mg/kg to about 50 mg/kg. Typically, dosage levels on the order of about 0.1 mg to about 10,000 mg of the inhibitor are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex, and diet of the patient; the time of administration; the rate of excretion; any combination of the compound with other drugs; the severity of the particular disease being treated; and the form and route of administration. Typically, in vitro dosage-effect results provide useful guidance on the proper doses for patient administration. Studies in animal models can also be helpful. The considerations for determining the proper dose levels are well-known in the art.

In the methods of the present invention, the composition may be administered, for example, orally, parenterally, by inhalation spray, topically, rectally, nasally, buccally, sublingually, vaginally, intraventricularly, or via an implanted reservoir in dosage formulations containing conventional non-toxic pharmaceutically-acceptable carriers, adjuvants and vehicles.

The compositions used in the methods of the present invention may be administered by a single dose, multiple discrete doses or continuous infusion. Any administration regimen regulating the timing and sequence of delivery of the compound can be used and repeated as necessary to effect treatment. Such regimen may include pretreatment and/or co-administration with additional therapeutic agents.

To maximize protection of tissue damage, the composition of the invention should be administered to the affected cells as soon as possible.

In a sixth aspect the present invention relates to the use of an inhibitor as described above, a nucleic acid encoding thereof, or a nucleic acid vector comprising said nucleic acid for the manufacture of a medicament for the prevention or treatment of a subject suffering of from a disease associated with PARP activation.

The inhibitors of the invention inhibit PARP activity and, thus, are believed to be useful for treating tissue damage resulting from cell damage or death due to necrosis or apoptosis, neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, immune senescence, inflammatory disorders like inflammatory bowel disorders such as colitis and Crohn's disease, muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize tumor cells.

The present invention will be understood more clearly on reading the description of the experimental studies performed in the context of the research carried out by the applicant, which should not be interpreted as being limiting in nature.

EXAMPLES

1) Plasmid Construction

The cDNA clones corresponding to the complete coding sequence from H2A (NM_138609; nucleic acid 186 to 1295 of SEQ ID NO: 4), macroH2A1.1 (NM_004893; nucleic acid 174 to 1289 of SEQ ID NO: 5) and macroH2A1.2 (NM_018649; nucleic acid 214 to 1332 of SEQ ID NO: 6) histones were PCR-amplified from image clones purchased from INVITROGEN with primers incorporating restriction enzyme recognition sites. The amplified PCR fragments were then subcloned into the Xho I-Not I sites of pREV-HTF retroviral vector or pGEX-5X.1 vector (AMERSHAM) according to the manufacturer's instruction. Constructs were sequenced to ensure sequence integrity.

2) Expression and Localization of MacroH2A1.1

MacroH2A1.1 and H2A histones were each stably expressed as fusion proteins with N-terminal double HA and double FLAG™ epitope tags (e-MH1.1, and e-H2A) in HeLa cells by retroviral transduction according to standard protocols. Immunofluorescence experiments were performed on stably transfected cells using Rat anti-HA antibody (ROCHE, 1:300 dilution), and a goat anti-rat IgG coupled to Alexa Fluor® 488 (MOLECULAR PROBES, 1:400 dilution) as a secondary antibody according to the manufacturers' instruction. The localization of chromatin was assessed in the same cells with DAPI coloration.

The results reveal that the tagged histones colocalize with chromatin (see FIG. 1), indicating that the presence of the tag epitopes do not interfere with their deposition. In contrast to tagged H2A histone (e-H2A), that shows a broad staining in the nucleus, tagged macroH2A1.1 histone (e-MH1.1) shows a localized staining restricted mainly to condensed chromatin. We conclude from these data that tagged macroH2A1.1 histone (e-MH1.1) and tagged H2A histone (e-H2A) are both functionally deposited into nucleosomes in vivo.

3) Purification of MacroH2A1.1 Associated Nucleosomes

The nuclear pellets prepared from the above described HeLa cells expressing the H2A and macroH2A1.1 proteins fused with N-terminal double-HA and double-FLAG epitope tags (e-H2A/e-MH1.1) were digested with micrococcal nuclease to give predominantly mononucleosomes as described in SOLLNER-WEBB and FELSENFELD {Biochemistry, vol. 14(3), p: 2915-20, 1975). Mononucleosomes containing e-H2A or e-MH 1.1 were purified from the resulting material by immunoprecipitation on anti-FLAG™ antibody-conjugated agarose (SIGMA). The bound nucleosomes were eluted with the FLAG peptide (DYKDDDDK; SEQ ID NO: 7), and were further affinity purified by anti-HA antibody-conjugated agarose (SIGMA) and eluted with the HA peptide (YPYDVPDYA; SEQ ID NO: 8). A small fraction of the purified complexes has been analyzed with an anti-FLAG™ antibody (ROCHE) on SDS-PAGE gel to assess for its enrichment in tagged macroH2A1.1 and H2A histones.

Figure 2:
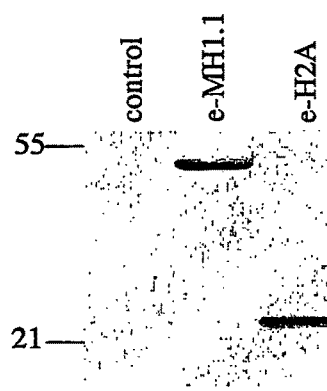
FIG. 2 shows the signal obtained with anti-FLAG™ antibody after immunoblotting of purified nuclear complexes from HeLa cells expressing the tagged H2A (e-H2A) and macroH2A1.1 (e-MH1.1) histones.

The immunoblotting with anti FLAG™ antibody revealed one specific band at the expected size for tagged macroH2A1.1 or H2A histones (see FIG. 2). The biochemical fractionation has revealed that only a small fraction of macroH2A1.1 histone was found to be present as a soluble protein in the nuclear extract, and that most of the protein was found to be present in the nuclear pellet tightly associated to chromatin. We have found that tagged macroH2A1.1 histone can be efficiently solubilized together with mononucleosomes by digesting chromatin with controlled amount of micrococcal nuclease.

Then, the purified complexes containing tagged macroH2A1.1 or H2A histones were run on 12% denaturating polyacrylamide gel, which was silver stained using SilverQuest® kit (INVITROGEN) according to the manufacturer's instruction. Finally, the different gel separated polypeptides were identified by mass spectrometry. As a control, we performed the same purification on untransduced HeLa cells.

Figure 3:
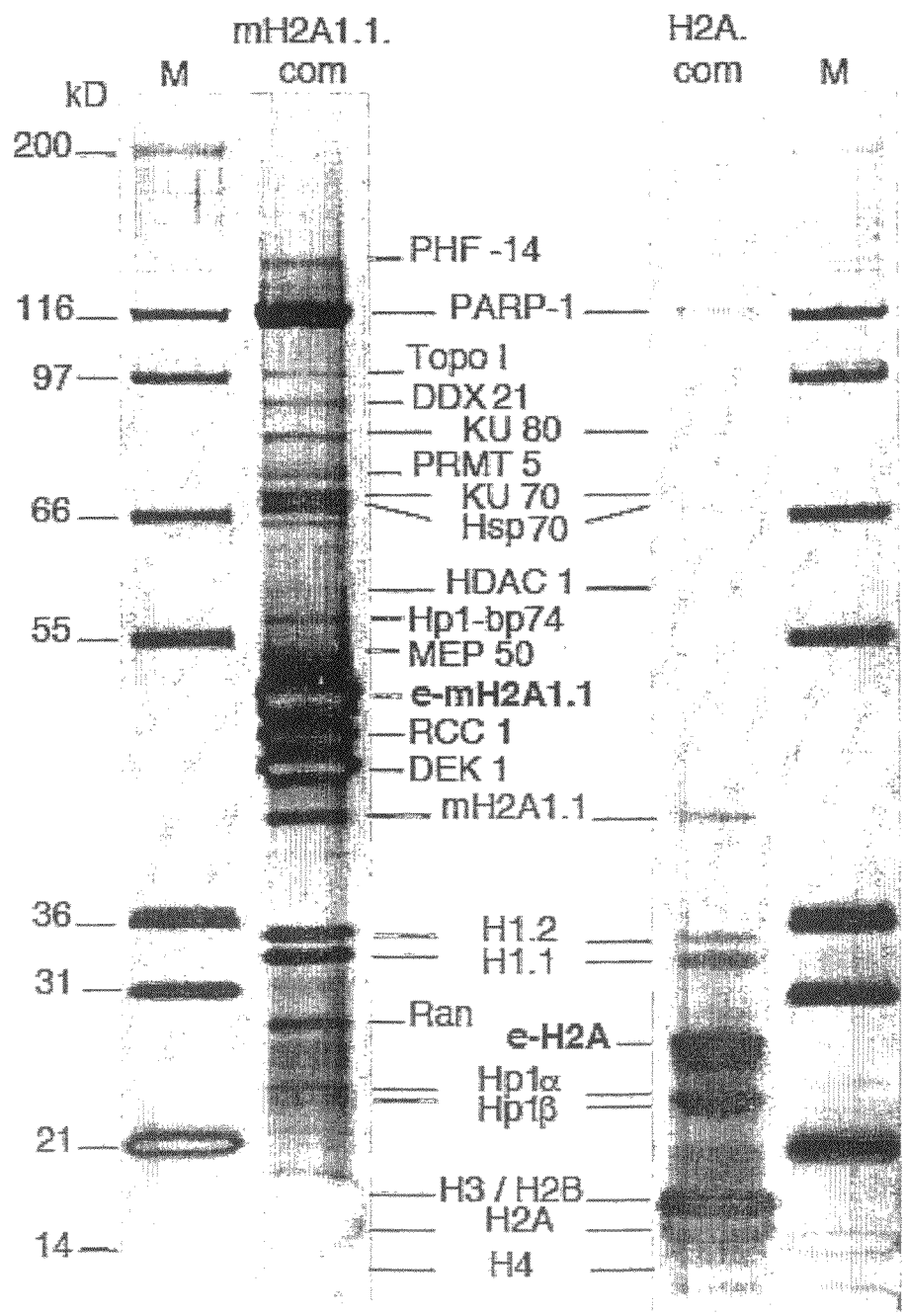
FIG. 3 shows the silver staining of the separating polyacrylamide gel of anti-FLAG/HA immunoprecipitation from nuclear extracts of Hela cells expressing tagged H2A (H2A com), and MacroH2A1.1 (MH1.1 corn) histones respectively. The polypeptides identified by mass spectrometric analyses are indicated. M corresponds to the M12 protein molecular weight marker (INVITROGEN).

Numerous polypeptides were found associated with e-mH2A1.1 and e-H2A nucleosomes (FIG. 3).

Mass spectrometric analyses, identified histones H3, H4, H2A, H2B, mH2A1.1 Ku 80, KU 70, Hsp70, HDAC1, the two subtypes of H1 (H1.1 and H1.2), Hp1α, Hp1β and poly (ADP-ribose) polymerase I (PARP-1) as common components in both e-mH2A1.1 and e-H2A complexes (FIG. 3). A comprehensive list of the identified proteins, with their accession numbers, is presented in the following table.

List of proteins associated with H2A and mH2A1.1 nucleosome complexes.

| H2A | mH2A1.1 | Accession numbers |
|---|---|---|
|  | PHF-14 | O94880 |
| PARP-1 | PARP-1 | P09874 |
|  | Topo I | P11387 |
|  | DDX 21 | Q9NR30 |
| KU 80 | KU 80 | P13010 |
| KU 70 | KU 70 | P12956 |
|  | PRMT5 | AAH25979 |
| Hsp 70 | Hsp 70 | P17066 |
| HDAC1 | HDAC1 | Q13547 |
|  | Hp1-bp 74 | CAI12528 |
|  | MEP 50 | Q9BQA1 |
|  | RCC 1 | P18754 |
|  | DEK | P35659 |
| mH2A1 | mH2A1 | O75367 |
| H1.2 | H1.2 | P16403 |
| H1.1 | H1.1 | Q02539 |
|  | Ran | P62826 |
| Hp1α | Hp1α | P45973 |
| Hp1β | Hp1β | P83916 |
| H3 | H3 | AAI08702 |
| H2B | H2B | CAB02542 |
| H2A | H2A | CAG33360 |
| H4 | H4 | CAG46986 |

Although, both complexes were found to contain PARP-1, only the e-mH2A1.1 complex had a significant amount of PARP-1.

Figure 14:
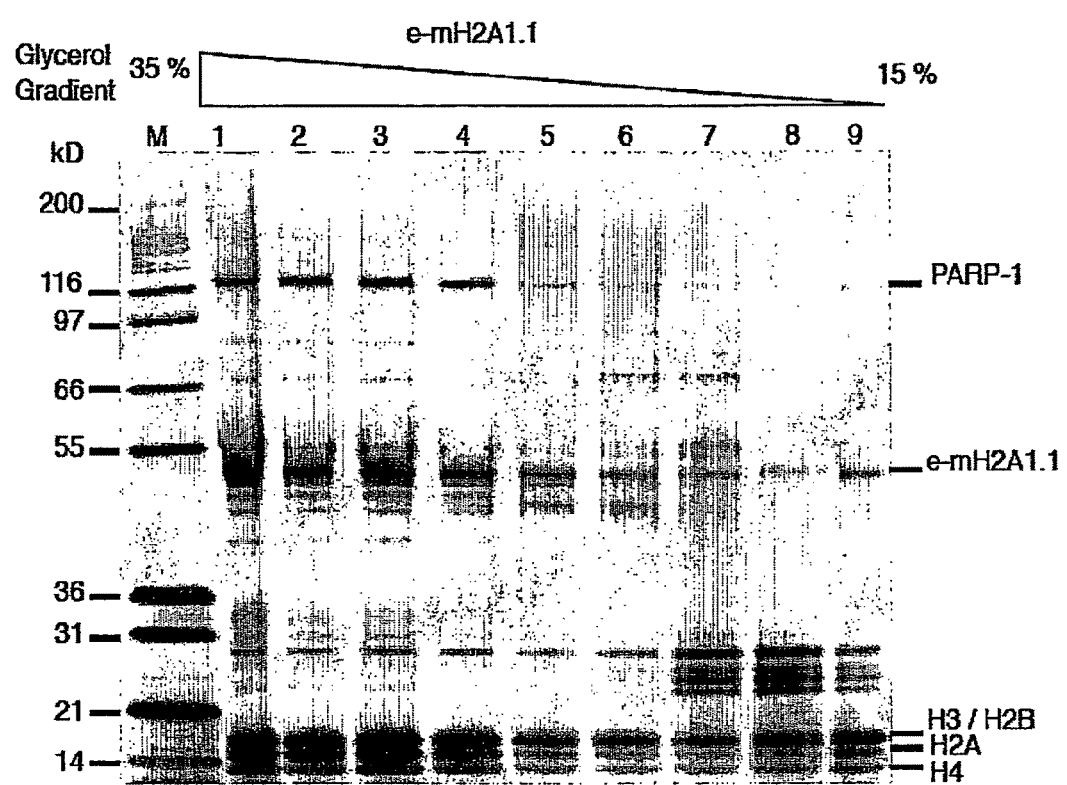
FIG. 14 shows the stable association of PARP-1 with the e-mH2A1.1 complex after isolation of said complex on a 15-35% glycerol gradient, fractionation of said gradient and loading of fractions (1 to 9) on a 4-12% SDS PAGE. The positions of the core histones, e-mH2A1.1 and PARP-1 were indicated at the left part of the figure. M, molecular mass marker.

A part of the purified complex was run on a 15-35% glycerol gradient, the gradient was fractionated and the different fractions were loaded an a 4-12% SDS-PAGE. The positions of the core histones, e-mH2A1.1 and PARP-1 are indicated at the left part of the FIG. 14.

Finally, the amount of PARP-1 present in the complex was found to be proportional to the amount of e-mH2A1.1 and histone H4 (FIGS. 3 and 14) suggesting a direct interaction between mH2A1.1 and PARP-1. In contrast, the H2A complex contained ~10 times less PARP-1 (the ratio between PARP-1 and histone H4 was found to be close to 0.1, FIG. 3, right panel). No polypeptides were detected by silver staining from the mock purification of untransduced HeLa cells (data not shown), indicating that all detectable polypeptides in these complexes are specific to macroH2A1.1 or H2A histones.

4) MacroH2A1.1 Interacts with PARP-1 Through its C-Terminal Non-Histone Region

To confirm the interaction between macro-H2A1.1 histone and PARP-1, we performed a GST-pull down experiment using a recombinant macroH2A1.1 as bait. Histone H2A and GST were used as controls. GST fusion histones were expressed in BL21 (pLysS) *E. Coli* strain grown at 25° C. The soluble proteins were purified on glutathione Sepharose™ 4B beads (AMERSHAM) according to the manufacturer's instruction. Human recombinant PARP-1 (ALEXIS) was incubated for 1 h with the recombinant GST fused or not with H2A histone (GST-H2A), macroH2A1.1 histone (GST-macroH2A1.1), or to the non histone region (NHR; amnion acids 121 to 369 of SEQ ID NO:1) of macroH2A1.1 (GST-NHR), at 30° C. with gentle mix in PBS with 100 mM KCl and 0.02% NP40 (SIGMA). After a washing step, the bounded proteins were eluted in LAEMMLI's buffer, fractionated on a 12% SDS-PAGE protein gel, blotted and then revealed by a human anti-PARP-1 antibody (ALEXIS).

Figure 4:
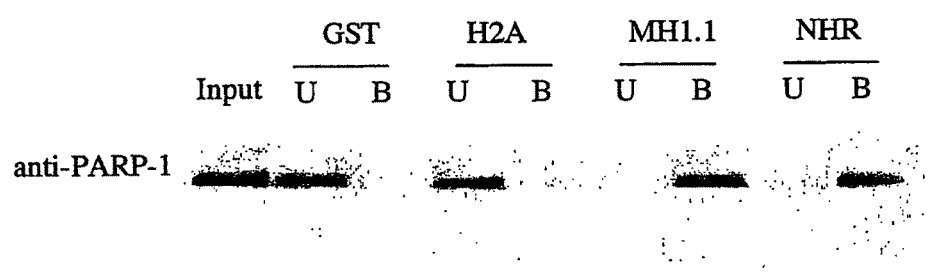
FIG. 4 shows the Human recombinant PARP-1 protein in bounded (B) and unbounded (U) fraction to the recombinant GST (GST), GST-H2A (H2A), GST-macroH2A1.1 (MH1.1) or GST-NHR (Non Histone Region) proteins.

The results show that the recombinant macroH2A1.1 histone interacts specifically with PARP-1 through its non histone region (NHR), and that this interaction did not depend on the presence of DNA (see FIG. 4). The C-terminal non-histone region macroH2A1.1 comprises a C-terminal region without any homology with other proteins (residue 121 to 201) and the macro domain. Thus, these results suggest that this C-terminal region, which if macroH2A1.1 specific is a good candidate as PARP-1 binding site.

5) Identification of MacroH2A1.1 Target Genes

Figure 5:
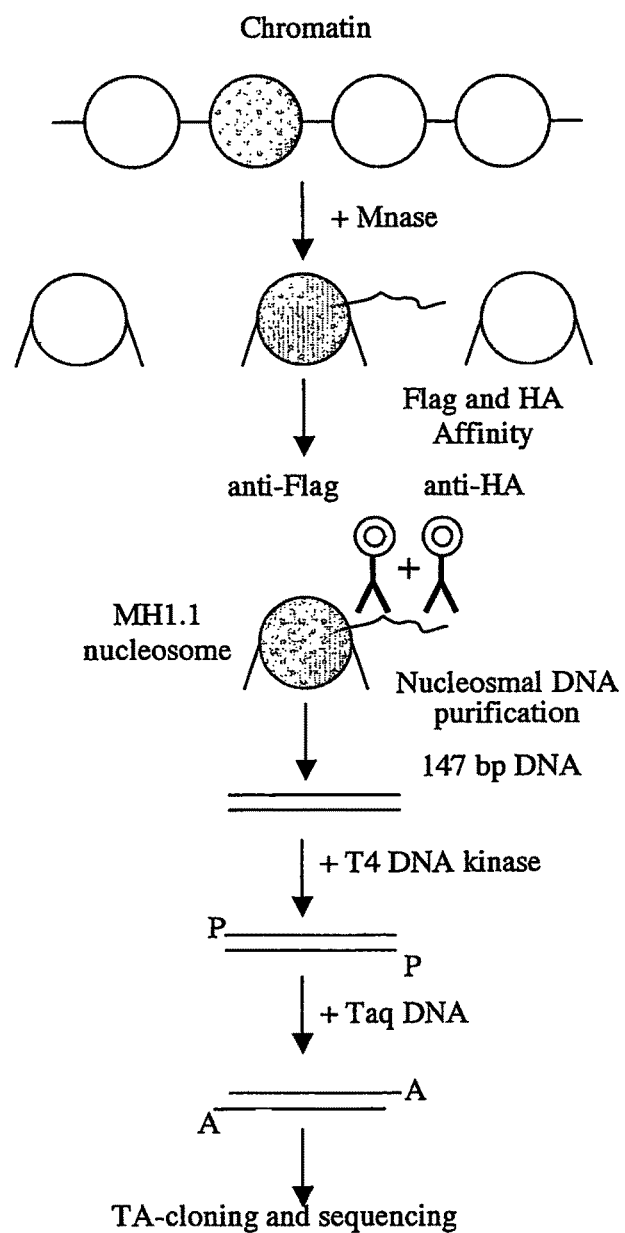
FIG. 5 described the different steps of the Tap-Chip method. The purified chromatin is digested with micrococcal nuclease (Mnase). Then, the nucleosomes containing the tagged macro-H2A1.1 histone were purified by immunoprecipitation with anti-HA and anti-FLAG™ antibodies. DNA is then purified and phosphorylated with T4 DNA kinase. An adenosine nucleotide is added to the 3' position of the fragment with Taq polymerase, and the obtained fragment is finally cloned in a plasmid for further sequencing.

A number of studies suggest a general involvement of macroH2A histone in heterochromatin establishment or maintenance. These data strongly support an involvement of macroH2A histone in transcription repression, but the mechanism by which this repression is achieved is unknown. These studies used mainly the immunofluorescence approach and failed to identify specific macroH2A histone target genes. To address this question, we have developed a highly specific chromatin immunoprecipitation assay that uses the tandem-affinity purification method to identify specific target DNA sequences associated with macroH2A1.1 nucleosomes. We called this approach "Tap-Chip" (see FIG. 5), for "Tandem Affinity Purification and Chromatin ImmunoPrecipitation assay". Our approach did not use formaldehyde crosslinking or PCR amplification, which have the inherent risk of artifacts.

We purified the nuclei from HeLa cell line stably expressing tagged macroH2A1.1 histone according to standard methods. The purified nuclei were digested with controlled amount of micrococcal nuclease to give predominantly mono- and dinucleosomes (data not shown). The digested chromatin was found to contain a significant amount of the tagged macroH2A1.1 histone (data not shown). MacroH2A1.1 mono- and dinucleosomes were immunopurified with (i) an anti-FLAG™ antibody, and then with (ii) an anti-HA antibody as above described. A small fraction of the purified mono- and dinucleosomes has been analyzed on SDS-PAGE gel to assess for its enrichment in tagged macroH2A1.1 histone (data not shown). As a control, we performed mock purification from a non-tagged HeLa cell line, and no polypeptides can be detected by silver staining (data not shown).

Immunopurified macroH2A1.1 mono- and dinucleosomes were digested with proteinase K, and phenol extracted according to standard methods. The purified DNA was treated with T4 DNA kinase (BIOLABS) and a 3' A-overhangs were added using Taq DNA polymerase (AMERSHAM). DNA Fragments corresponding to macroH2A1.1 mono- and dinucleosomes were cloned into pcDNA™3.1 TOPO® vector using TA cloning technology (INVITROGEN). The transformed clones were checked for inserts and sequenced by using vector-specific primers. The sequences obtained were then identified by Blast search of the human genome database (www.ncbi.nlm.nih.gov/).

The results in the literature show that MacroH2A is associated to gene repression and localize essentially to the inactive X-chromosome where it contributes to X inactivation. Interestingly, our results show that that macroH2A is not restricted to the X-chromosome but it is widespread along the genome. 45% of the 60 identified genes are enzymes, and the others are involved in different biological pathways. Moreover, the analysis of these identified genomic sequences revealed that macroH2A1.1 histone associates mainly with promoter regions of several highly regulated genes, and then could be involved in the general regulation of inducible or early responsive genes.

One of the identified genomic sequence corresponds to hsp70-1 promoter gene. Hsp70-1 (or hsp70i) is one of the most prominent and best characterized member of the family hsp70 family, which encompasses at least 11 genes, and encodes a group of highly related proteins (TAVARIA et al., 1996). Hsp70-1 is inducible in response to heat shock and chemical stresses and the probe used here picks up specifically this gene.

6) MacroH2A1.1 Targets Specifically the hsp70 Promoter

In order to confirm the association of macroH2A1.1 histone with gene promoters, we analyzed its distribution on the hsp70-1 locus using semi-quantitative and real time PCR. The chromatin from Hela cells expressing tagged macroH2A1.1 histone (e-MH1.1) was precipitated as described bellow, with anti FLAG™ and anti-HA antibodies. The chromatin was cross-linked with formaldehyde solution for 10 min at 37° C., and then sonicated to obtain an average length of 300 to 800 bp DNA fragments. The extracts were standardized by non-denaturing gel electrophoresis and each sample was analyzed independently by semi-quantitative PCR with the following primers:

```
hsp70-1 promoter (forward):
5'-GGCGAAACCCCTGGAATATTCCCGA-3';   (SEQ ID NO: 9)

hsp70-1 promoter (reverse):
5'-AGCCTTGGGACAACGGGAG-3';         (SEQ ID NO: 10)

hsp70-1 coding region (forward):
5'-CAGGTGATCAACGACGGAGACA-3';      (SEQ ID NO: 11)

hsp70-1 coding region (reverse):
5'-GTCGATCGTCAGGATGGACACG-3'.      (SEQ ID NO: 12)
```

Semi-quantitative PCR were performed with Taq DNA polymerase (PROMEGA) on the hsp70.1 promoter and coding region using the oligonucleotide pairs described below. Samples were amplified for 25 cycles (93° C. for 30 sec, 58° C. for 30 sec, and 72° C. for 1 min), and run on 2% agarose gels, visualized with ethidium bromide and quantified by densitometry.

Figure 6:
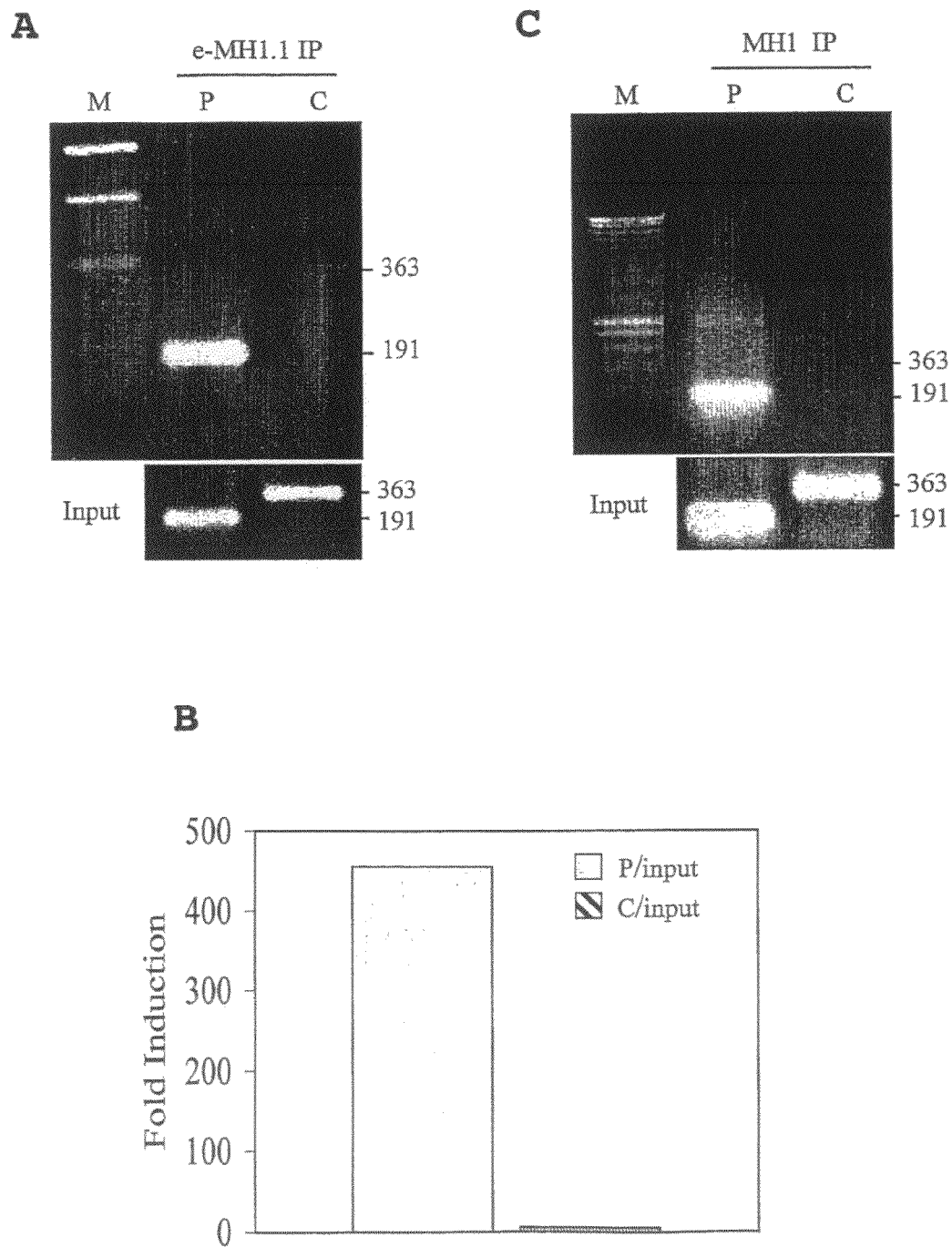
FIG. 6A shows the PCR amplification products obtained with hsp70-1 promoter (P) and coding (C) region primers from one extract of immunoprecipitated chromatin from Hela cells stably expressing tagged macro-H2A1.1 histone. Control amplification have been done with the same primers on chromatin from Hela cells before immunoprecipitation (input). Lane M correspond to a molecular ladder (1,000 pb ladder, INVITROGEN).
FIG. 6B show the relative enrichment of macroH2A1.1 histone on promoter region (gray) versus the coding region (hatched) of hsp70-1 gene in Hela cells.
FIG. 6C shows the PCR amplification products obtained with hsp70-1 promoter (P) and coding (C) region primers from one extract of macroH2A1.1 histone immunoprecipitated chromatin from non-transfected Hela cells. Lane M correspond to a molecular ladder (1,000 pb ladder, INVITROGEN).

The results show that the DNA fragment spanning the hsp70-1 promoter (P, 191 bp) was enriched, whereas the fragment located in the coding region (C, 363 bp) was not (see FIG. 6A). These results demonstrate that macroH2A1.1 is present at the hsp70-1 promoter.

We then used a real-time PCR to quantify the relative enrichment of macro-H2A1.1 histone in the promoter region using a LightCycler® (ROCHE DIAGNOSTICS). Two different dilutions of each sample were analyzed independently by Q-PCR with the aforementioned primers and GAPDH primers for normalization (GAPDH (forward): 5'-GGA CCT GAC CTG CCG TCT AGA A-3' (SEQ ID NO: 13); GAPDH (reverse): 5'-GGTG TCG CTG TTG AAG TCA GAG-3' (SEQ ID NO: 14). The copy numbers were calculated as described in FERREIRA et al. (2001), and the results from Q-PCR were presented as the ratio between Hsp70 mRNA versus GAPDH mRNA. Finally, the PCR values were normalized against values obtained with chromatin from non-transfected cells.

The results show that MacroH2A1.1 was found to be enriched 450 times on the promoter region of the hsp70-1 gene compared to the coding region (see FIG. 6B).

We then asked if the ectopically expressed macroH2A1.1 histone adequately reflects the distribution of native protein throughout the genome and hence the target genes identified by our TAP-ChIP approach are indeed the real in vivo targets of macroH2A1.1 histone. To determine whether the hsp70-1 promoter is a bona fide target of macroH2A1.1, we examined the in vivo distribution of the endogenous macroH2A1.1 histone on the hsp70-1 promoter using a non-transfected HeLa cell line. In vivo chromatin immunoprecipitation (ChIP) assays were performed as described previously using a polyclonal antibody directed against the non-histone region of histone macroH2A1.1. The extracts were standardized by non-denaturing gel electrophoresis and each sample was analyzed independently by semi-quantitative PCR as described previously.

The results show that the DNA fragment spanning the hsp70-1 promoter (P) was enriched after coimmunoprecipitation of chromatin with a macroH2A1.1 specific antibody in three independent ChIP assays, whereas a fragment located in the coding region (C) was not (see FIG. 6C). These results demonstrate that macroH2A1.1 is naturally present in vivo at the hsp70-1 promoter.

We next asked if mH2A1.1 was associated with the promoters of other inducible genes of the Hsp70 family as well as with constitutively expressed Hsp70 genes. We used a candidate approach, focusing on the heat shock-inducible Hsp70.2 and the constitutively expressed Hsp70.8 (Hsc70) genes (Dworniczak and Mirault 1987).

A ChIP assay using the anti-FLAG™ and anti-HA antibodies was carried out with formaldehyde cross-linked chromatin isolated from HeLa cell lines stably expressing e-mH2A1.1 as described previously.

Finally, Real-time PCR quantification was realized as described previously using primers specific for the respective promoters, which were as follows:

```
Hsp70.2 promoter (forward):
5'-GGCCGAGAGTCAGGGAGGAACC-3';     (SEQ ID NO: 24)

Hsp70.2 promoter (reverse):
5'-ACTCTTCCAGCTCCACCACAG-3';      (SEQ ID NO: 25)

Hsp70.8 promoter (forward):
5'-TGTGGCTTCCTTCGTTATTGGA-3';     (SEQ ID NO: 26)

Hsp70.8 promoter (reverse):
5'-AAATACCGCTGCCATCCCACCG-3'.     (SEQ ID NO: 27)
```

Figure 13:
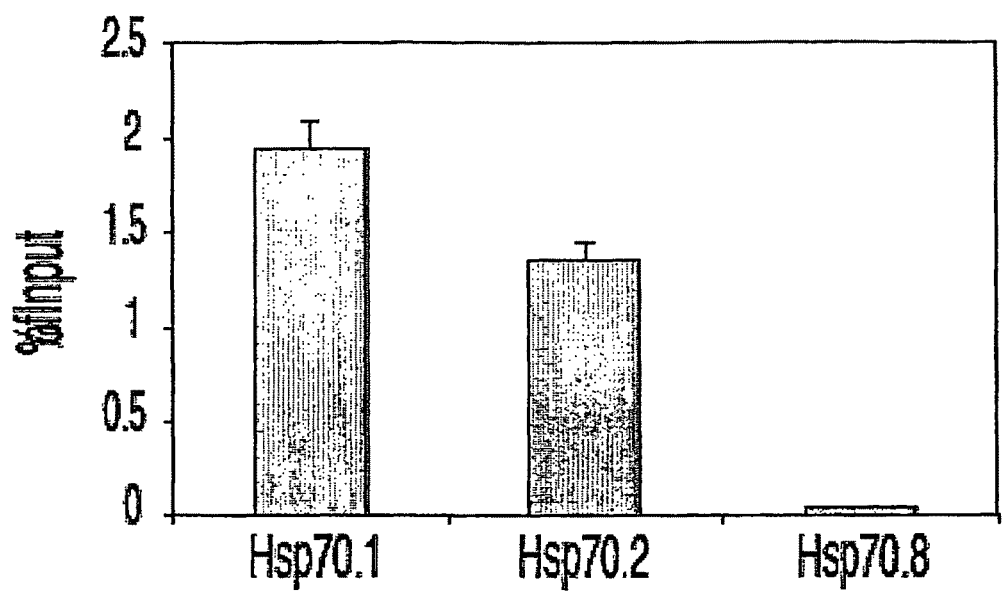
FIG. 13 shows the amount of DNA immuno-precipitated with Hsp70.1, Hsp70.2 or Hsp70.8 promoter's probe as a function of percent input DNA.

The results clearly show that the promoter region of the Hsp70.2 gene was enriched in e-mH2A1.1 to an extent similar to that of the Hsp70.1 gene, whereas the presence of e-mH2A1.1 was barely detectable at the promoter of the Hsp70.8 gene (FIG. 13). These data suggest that mH2A1.1 may in general be preferentially associated with inducible heat shock genes.

7) Heat Shock Induced MacroH2A1.1 and PARP-1 Displacement from the Hsp70-1 Promoter Intending to comprehensively describe the function of macroH2A1.1 in gene regulation and its relationship with PARP-1, we have examined the order of events occurring at the hsp70-1 promoter during heat shock dependent transcriptional activation. Different HeLa cell lines expressing a FLAG-HA tagged versions of macro-H2A1.1, H2A, H3 or H3.3 histones were established. A non-tagged HeLa cell line was used as a negative control. The expression of hsp70-1 gene was induced by heat shocking HeLa cells at 42° C. for 30 min and a ten fold induction was routinely observed (data not shown). The cells were left to recover for 30 min and immediately treated with formaldehyde to cross-link protein-protein and protein-DNA complexes. Sheared chromatin was then precipitated as described previously using anti FLAG™ antibody for macroH2A1.1, H2A, H3 and H3.3 histones. In parallel, we also examined with specific antibodies the presence of the histone-modifying enzyme PARP-1 (ALEXIS), the ADP-ribose polymers (ALEXIS) and pan-acetylated histone H4 (ALEXIS). As a control, chromatin was immunoprecipitated in the absence of specific antibodies. Standardization of the chromatin inputs for immunoprecipitation was assessed in each experiment using real time PCR. Levels of GAPDH, which is constitutively expressed, were also evaluated as a negative control, and as expected the sequence was found to be barely detectable in the immunoprecipitates. The hsp70-1 promoter fragment in the immunoprecipitates was quantified using real time PCR as described previously.

Figure 7:
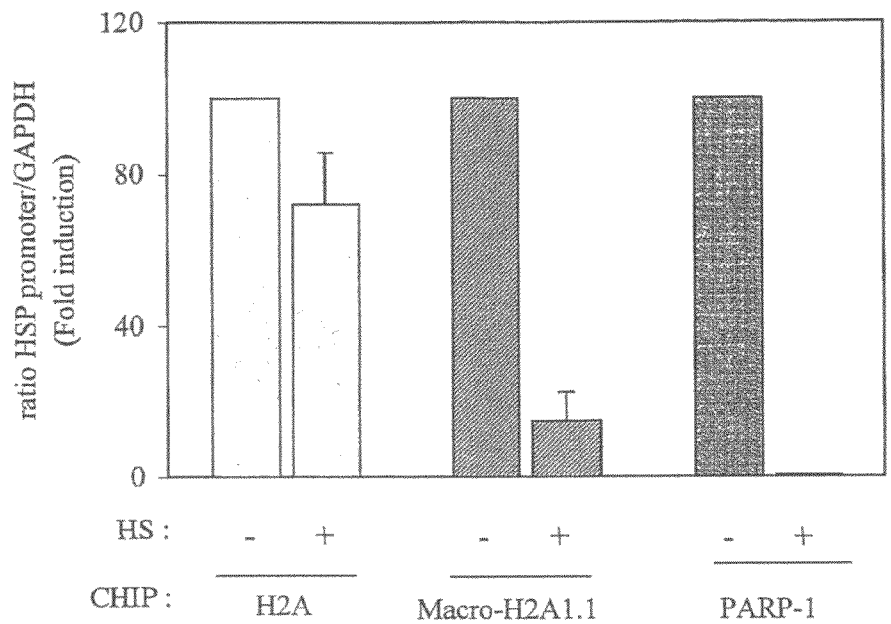
FIG. 7A shows the quantity of H2A or macroH2A1.1 histones, or of PARP-1 on hsp70-1 promoter versus GAPDH promoter in Hela cells after a heat shock (HS, +) or without any heat shock (−). Each result corresponds to the mean of three independent experiments.
FIG. 7B shows the quantity of H3 or H3.3 histones, and of PARP-1 on hsp70-1 promoter versus GAPDH promoter in Hela cells after a heat shock (HS, +) or without any heat shock (−). Each result corresponds to the mean of three independent experiments.
Figure 7:
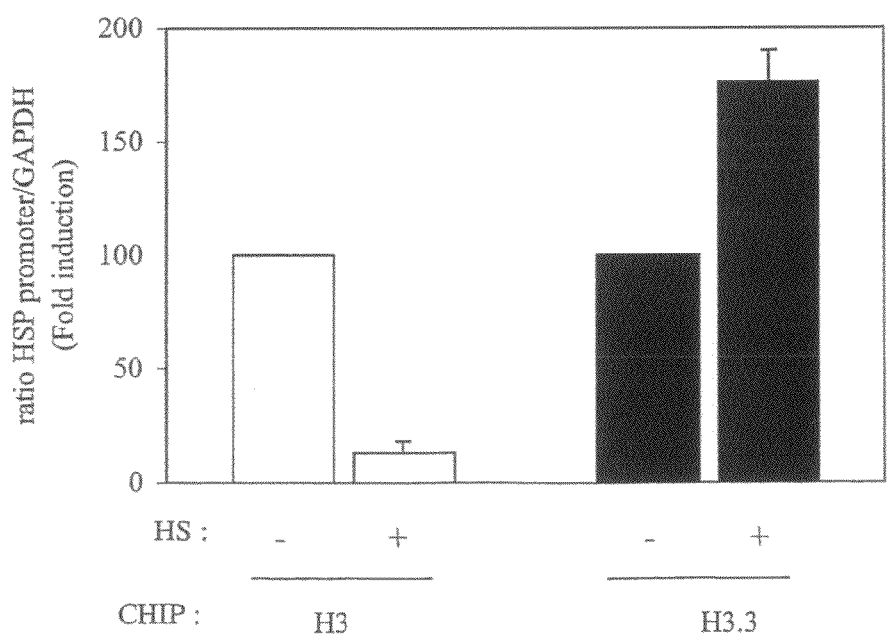
Figure 8:
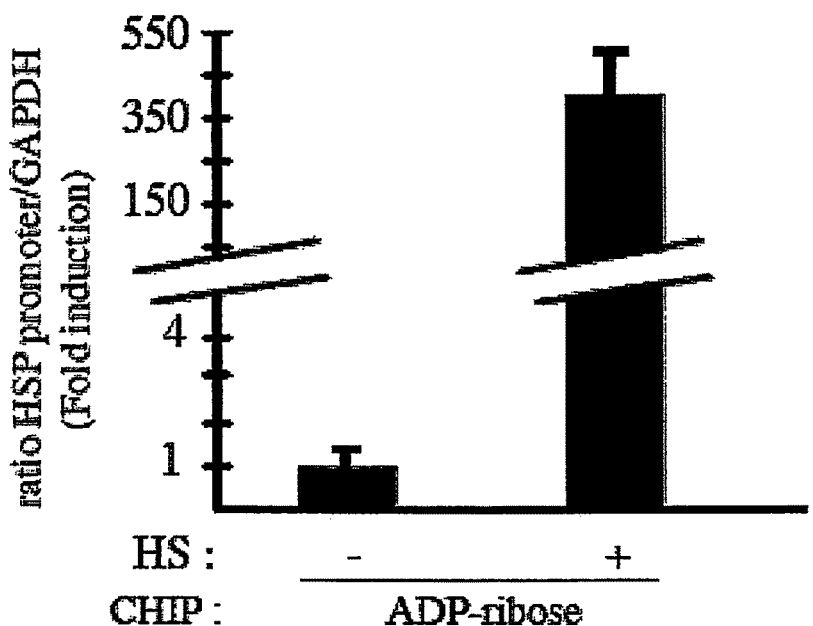
FIG. 8A shows the quantity of ADP-ribose on hsp70-1 promoter versus GAPDH promoter in Hela cells after a heat shock (HS, +) or without any heat shock (−). Each result corresponds to the mean of three independent experiments.
FIG. 8B shows the quantity of acetylated H4 histone on hsp70-1 promoter versus GAPDH promoter in Hela cells after a heat shock (HS, +) or without any heat shock (−). Each result corresponds to the mean of three independent experiments.
Figure 8:
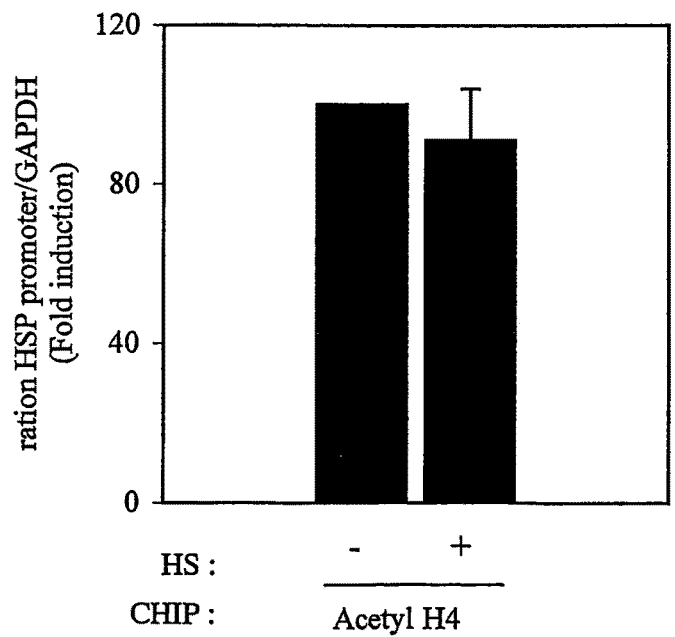

The results show that macroH2A1.1 and PARP-1 are present on the hsp70-1 promoter before activation and that heat shock induced their displacement from the promoter (see FIG. 7A). The association of macro-H2A1.1 with hsp70-1 promoter dropped by 90%, while the canonical H2A histone was only slightly affected (less then 30% drop). Interestingly, PARP-1 was almost not detectable on the hsp70-1 promoter after heat shock (see FIG. 7A) since a high level of poly(ADP-ribose) polymers appeared at the time of activation (see FIG. 8A)). Consistent with recent findings, H3.3 histone was found to replace H3 histone in the transcriptionally active hsp70-1 promoter (see FIG. 7B). In contrast, we found no changes in global H4 histone acetylation (see FIG. 8B). These observations suggest that PARP-1 ADP-ribosylation activity is inhibited, while it is sequestered by macro-H2A1.1 on the promoter. PARP-1 becomes active when it is released from the promoter, and modifies local proteins, leading to an accumulation of ADP-ribose moieties.

Since ADP-ribosylation is essential for the release of chromatin bound proteins (for a recent review see (Kim et al. 2005), we hypothesized that both macroH2A1 and PARP-1 could be ADP-ribosylated.

Figure 15:
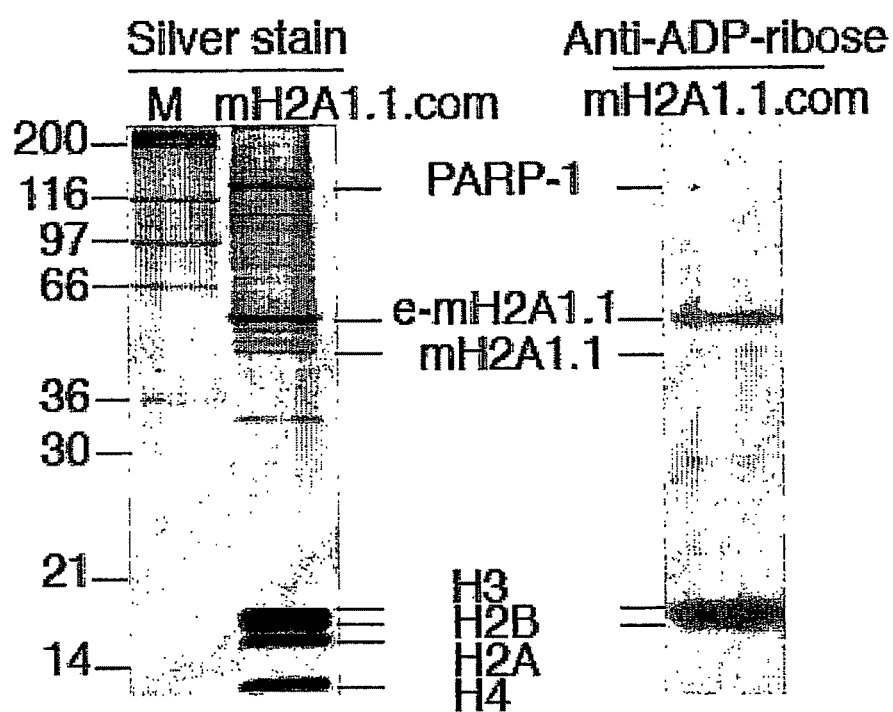
FIG. 15 shows isolated e-mH2A1.1 complex (com) after separation on a 12% PAGE, and silver stained (left panel), and western-blot of the complex revealed by anti-ADP ribose antibody (right panel). M, molecular markers with the molecular masses indicated at the left.

To visualize the association of the polymer with the proteins of the e-mH2A1.1 nucleosome complex in the absence of heat shock, we have isolated the e-mH2A1.1 complex from stable HeLa cell lines, separated on a 12% PAGE containing SDS, and silver stained (FIG. 15, left panel). Then, the gel was blotted and revealed by an anti-ADP ribose antibody (FIG. 15, right panel).

The Western blot showed that both PARP-1 and e-mH2A1.1 as well as the core histones H3 and H2B were ADP-ribosylated (FIG. 15, right panel), a result in agreement with the literature (Abbott et al., 2005). These results suggested that upon heat shock activation not only mH2A1.1 and PARP-1, but also the core histones should be heavily ribosylated and consequently released from Hsp70.1 promoter in an ADP-ribosylation dependent manner.

8) Down Regulation of MacroH2A1.1 or PARP-1 Delays Heat Shock Response

In order to address more precisely the role of macroH2A1.1 and PARP-1 in the hsp70-1 gene regulation, we designed two siRNAs corresponding to their specific mRNA sequences. The siRNA directed against macroH2A1 is located in the macro domain and it is shared by the two isoforms of macro-H2A1, i.e. macro-H2A1.1 and macro-H2A1.2. The siRNA directed against PARP-1 is located in the catalytic domain of PARP-1 (KAMEOKA et al., 2004). A scrambled sequence was used as a negative control (control siRNA). A search in sequence libraries indicated that our macro-H2A1 and PARP-1 siRNA are restricted to macro-H2A1 and PARP-1 respectively, and that the control siRNA sequence is absent altogether. The sequence of these siRNAs were as follow:

```
                                           SEQ ID NO: 15
    MacroH2A1 siRNA (MH1 siRNA,;
    5' AAGCAGGGUGAAGUCAGUAA 3'), SEQ ID NO: 16
    PARP1 siRNA (PARP-1 siRNA,;
    AAGCCUCCGCUCCUGAACAAU);

SEQ ID NO: 17
    Scrambled control siRNA (Scrambled siRNA,;
    5'-CAUGUCAUGUUCACAUCUCUT-3').
```

For siRNA transfection, HeLa cells in exponential growth were seeded onto E-well plates and grown overnight at 37° C. in DMEM/10% FBS (INVITROGEN). HeLa cells were transfected with Lipofectamine® (INVITROGEN) according to the manufacturer's instruction, and with 1 μg of each aforementioned siRNA, or no siRNA. 48 hours post-transfection, cells were heat-shocked at 42° C. for 60 minutes and left to recover at 37° C. for 10, 20 or 30 min. Cells were then harvested and assayed for hsp70.1 expression by RT-PCR. As a control, cells were also assayed for macro-H2A1 and PARP-1 silencing by immunoblotting.

Figure 9:
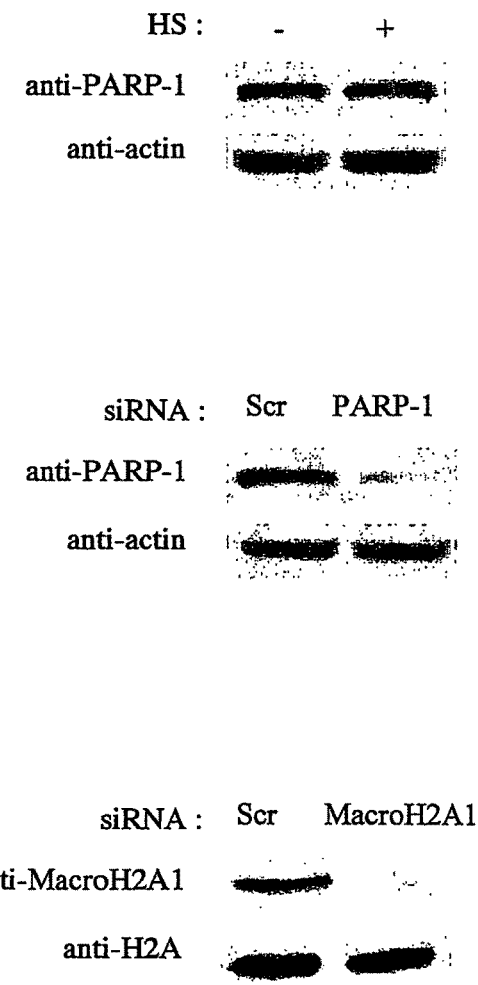
FIG. 9 shows the relative expression of PARP-1 30 in Hela cells minutes after a heat shock (HS, +) or without any heat shock (−), and in Hela cells transfected or not with a PARP-1 specific siRNA or an unrelated siRNA (Scr); and the relative expression of macroH2A1 in cells transfected or not with a macroH2A1 specific siRNA or an unrelated siRNA (Scr).

The results reveal that the expression of endogenous macroH2A1 and PARP-1 was almost completely inhibited (as revealed by western blot using specific antibodies against macroH2A1 and PARP-1, see FIG. 9). The results also reveal that the down regulation of macro-H2A1.1 or PARP-1 with specific siRNAs delayed the heat shock response respectively by 3 and 10 folds (see FIG. 10A). At the same time, HeLa cells transfected with a scrambled siRNA behaved as the control and did not show any delay in hsp70-1 activation.

In order to confirm this result, we performed a kinetic analysis of hsp70-1 activation in the presence of macroH2A1 siRNAs. HeLa cells transfected or not with macroH2A1 siRNA were heat shocked at 42° C. for 30 min and the expression of hsp70-1 was monitored by real-time RT-PCR after 10, 20 and 30 min recovery as previously.

Figure 10:
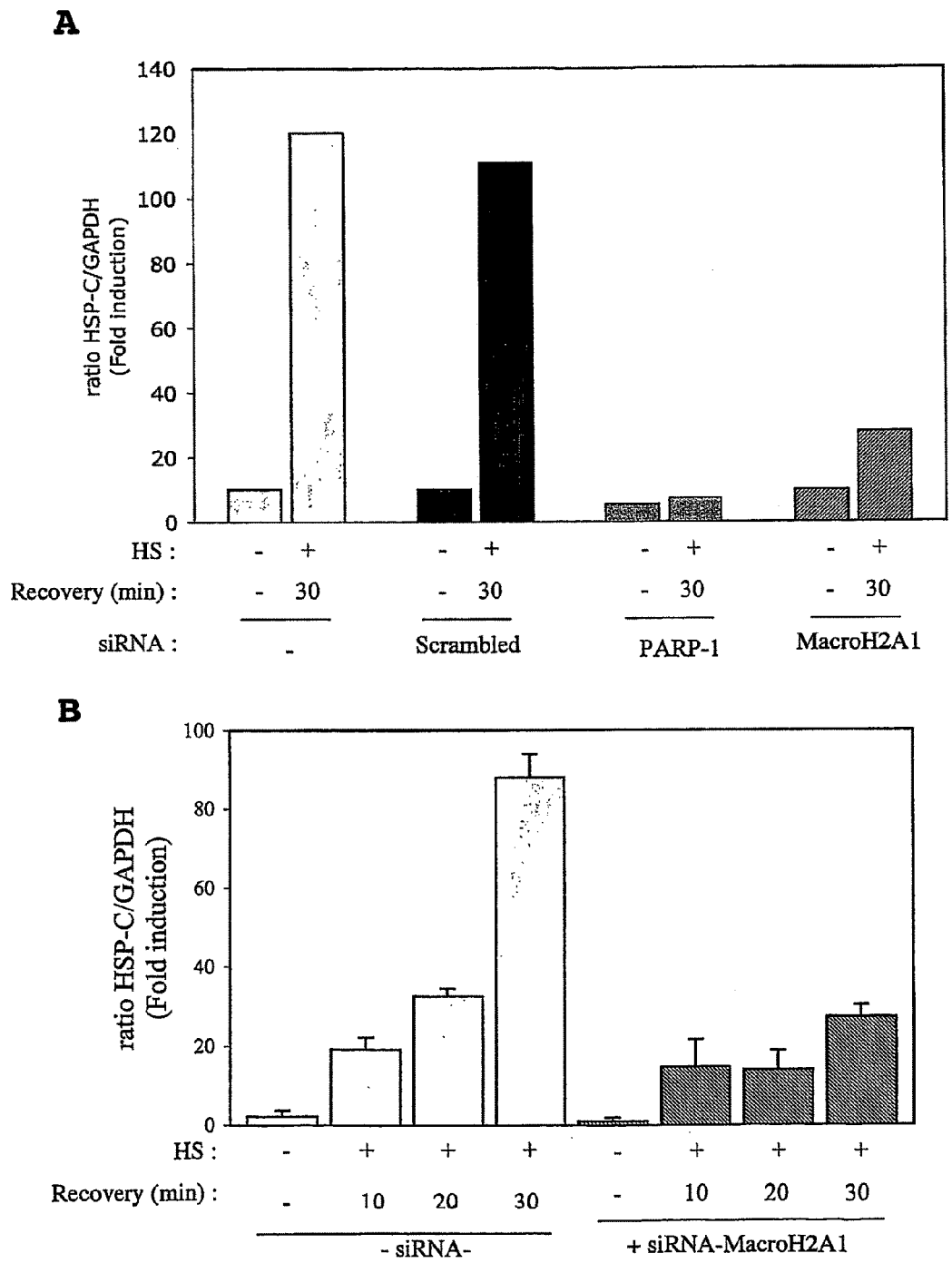
FIG. 10A shows the relative expression of hsp70-1 mRNA versus GAPDH mRNA 30 minutes in Hela cells after a heat shock (HS, +) or without any heat shock (−) by real-time PCR. Said cells have been transfected or not with unrelated siRNA (scrambled), PARP-1 specific siRNA (PARP-1), and macroH2A1 specific siRNA (MacroH2A1).
FIG. 10B shows a kinetic analysis by real-time PCR of hsp70-1 expression versus GAPDH expression in Hela cells transfected with macroH2A1 specific siRNA (+siRNA macro-H2A1) or without any siRNA (−siRNA macro-H2A1). Said assays were realized on transfected cells 10, 20 or 30 minutes after a heat shock (HS, +) or in the absence of any heat shock (−). The results are the mean of three independent experiments.
Figure 24:
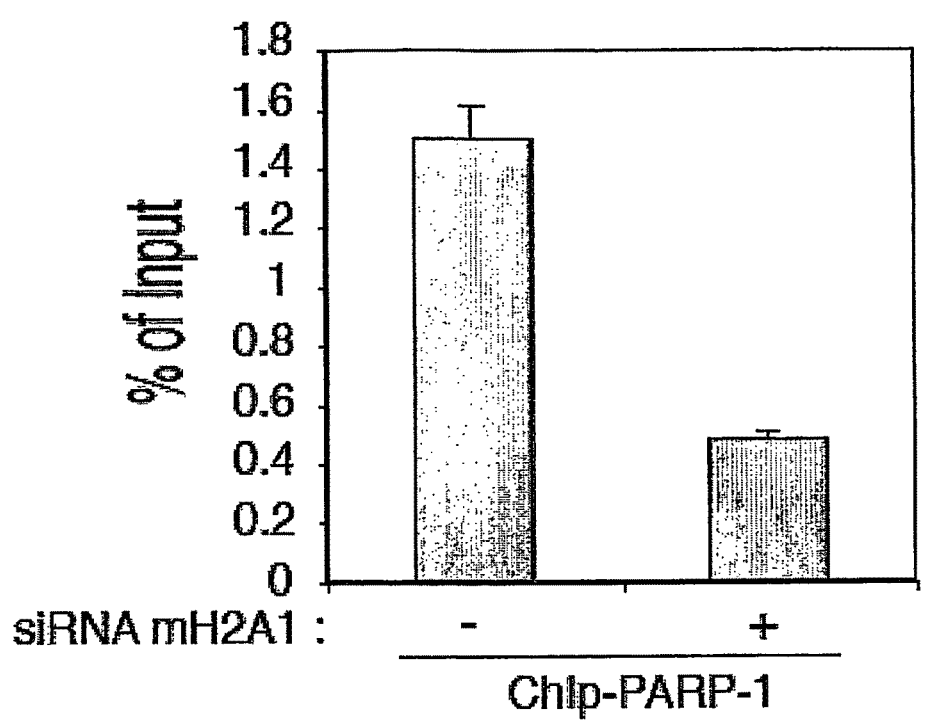
FIG. 24 shows that the suppression of the expression of mH2A1 with siRNA downregulates the amount of PARP-1 associated with the Hsp70.1 promoter. Control non-treated (−siRNA-mH2A1) and siRNA-treated (+siRNA-mH2A1) HeLa cells were crosslinked with formaldehyde and were used for ChIP with anti-PARP-1 antibody. DNA was isolated from both ChIP samples and submitted to real time PCR amplification with primers specific for the Hsp70.1 promoter.

The results clearly show that down regulation of macroH2A1.1 with a specific siRNA results in a delayed heat shock response by a three fold factor (see FIG. 10B). Since mH2A1 appeared to be involved in the association of PARP-1 with the Hsp70.1 promoter, one would expect that the depletion of mH2A1 by siRNA treatment would severely reduce the amount of Hsp70.1 promoter associated PARP-1, which, in turn, would interfere with the heat shock response. The ChIP data (FIG. 24) demonstrated that the depletion of mH2A1 resulted, as expected, in a strong decrease of the amount of PARP-1 interacting with the Hsp70.1 promoter.

Consistent with our results, PARP-1 was found to be required for heat shock-induced puffing and hsp70 expression in drosophila larvae (TULIN and SPRADLING, Science, vol. 299(5606), p: 560-2, 2003). Consequently, our results show that the macroH2A association with hsp70-1 promoter was clearly linked to its inactive state. The association with PARP-1 supports this view and suggests a role of macroH2A in the regulation of inducible genes that need to respond rapidly to hormones, cytokines, or heat shock. The identification of a large number of genes potentially regulated by macroH2A1.1 supports the notion that macroH2A1.1 is a central regulator that represses diverse cellular processes.

9) MacroH2A1.1 Regulates PARP-1 Enzymatic Activity

The physical association of macro-H2A1.1 with PARP-1 and their coordinated release from the hsp70-1 promoter after a heat-shock induced activation prompted us to examine the possible regulation of PARP-1 enzymatic activity by macro-H2A1.1. PARP-1 is known to auto-ADP-ribosylates itself and mechanisms controlling this auto-modification are not known.

Our results suggest that macroH2A is implicated in PARP-1 activity regulation. In order to elucidate this regulation process, we compared macroH2A sequences with proteins having a macro domain, and more specifically with phosphoesterases. In fact, ALLEN et al., (2003, aforementioned) suggests that the macro domain defines a superfamiliy of phosphoesterases that act on ADP ribose derivatives.

Our analysis shows that macroH2A1.1, macroH2A1.2, and macroH2A2 share an important homology with the catalytic domain of known phosphoesterases (see FIG. 11). Moreover, macroH2A1.1 and macroH2A2 share a phylogenetically invariant HXTX motif (in bold in FIG. 11 and FIG. 16) associated with the phosphoesterase activity (NASR and FILIPOWICZ, Nucleic Acids Res., vol. 28(8), p: 1676-83, 2000; HOFMAN et al., EMBO J., vol. 19(22), p: 6207-17, 2000), wherein the histidine residue is critical for activity. The corresponding residue in macroH2A1.2 is asparagine (N).

To test if a perturbation in the folding of mH2A1.1 may affect PARP-1 activity and facilitate the release of the otherwise mH2A1.1 nucleosome associated PARP-15 we have generated point mutation in the mH2A1.1 gene that convert at the conserved H, X, T, X motif at positions 213-216 to Alanines (A, A, A, A), and is referred hereafter as MH1.1mut (FIG. 16). Indeed, this H, X, T, X motif is present in other macro-domains that possess catalytic activity towards ADP-ribosylated substrates (FIG. 16 and Allen et al. 2003). It has previously been shown that the mutation of an analogous motif in a yeast phosphoesterase abolishes its enzymatic activity (NASR and FILIPOWICZ, 2000, abovementioned; HOFMAN et al, 2000, abovementioned). This motif is also in close proximity to the mH2A1.1 pocket (Allen et al. 2003; Chakravarthy et al. 2005), which binds ADP ribose (and possibly mono-ADP ribosylated PARP-1) and its derivative O-acetyl-ADPribose (Karras et al. 2005; Kustatscher et al. 2005), so that mutations in the motif may be expected to affect the binding.

Figure 17:
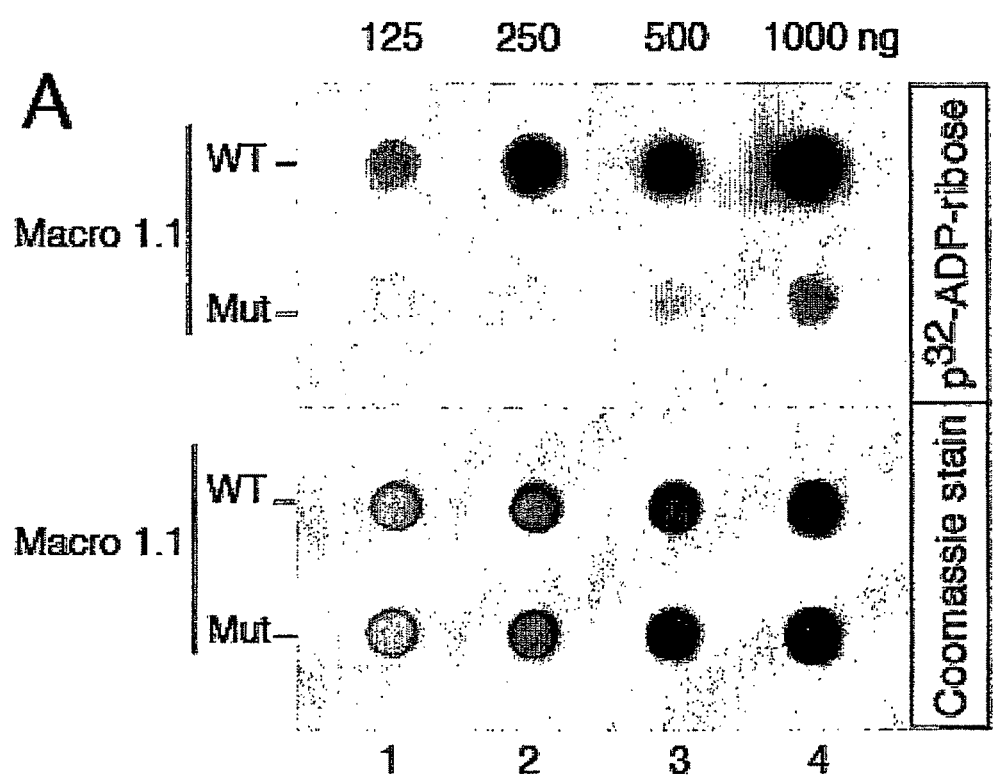
FIG. 17 shows the altered binding of mono-ADP-ribose to the mutated mH2A1.1. Recombinant wild type (WT) or the mutated (Mut) mH2A1.1 were purified to homogeneity. Increasing amounts of both proteins were loaded (in duplicate) on filters. One filter was then incubated with $^{32}$P-ADP-ribose (upper panel), whereas the other one was stained with Coommassie blue as a control for equal loading (lower panel).

To test if the above mutations affect the binding of mono-ADP-ribose, increasing amounts of recombinant wild type (WT) and mutated (Mut) mH2A1.1 macro domains were purified to homogeneity, incubated with $_{32}$P-ADP-ribose, and blotted (in duplicate) onto PVDF membranes to detect the labeled proteins (FIG. 17, upper panel). The duplicate membrane was Coomassie stained as a control for equal loading (FIG. 17, lower panel). The obtained results confirmed the weaker binding of mono-ADP-ribose to the mutated emH2A1.1 compared to its binding to the WT e-mH2A1.1 (FIG. 17, upper panel). This provides evidence that the structure of the e-mH2A1.1 pocket that binds ADP-ribose (Karras et al. 2005; Kustatscher et al. 2005) was perturbed in the mutated protein.

If the folding of mH2A1.1 is important for the affinity of PARP-1 binding within the e-mH2A1.1 nucleosome complex, alterations in the folding of e-mH2A1.1 should affect PARP-1 binding. To address this, we have purified wild type (WT) and mutated (Mut) emH2A1.1 complexes under different conditions of stringency, i.e. at 150 mM (FIG. 18, left panel) and 300 mM NaCl (FIG. 18, middle panel).

Figure 18:
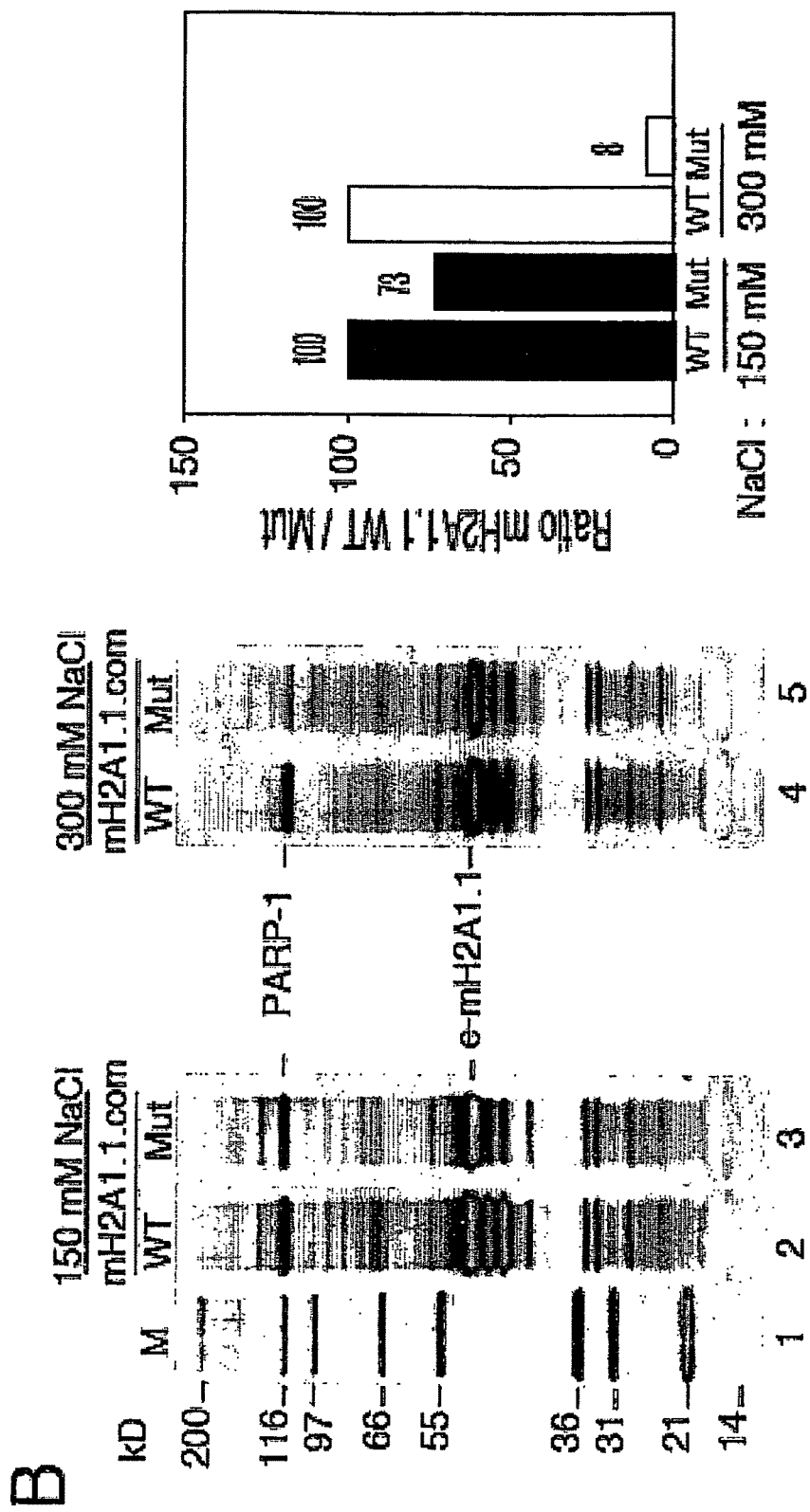
FIG. 18 shows that increasing the ionic strength releases the mutated, but not the WT e-mH2A1.1 protein, from the nucleosome complex. The wild type (WT) and mutated mH2A1.1 nucleosome complexes were isolated from cell lines stably expressing the WT or the mutated e-mH2A1.1 histone using either 150 mM NaCl (left panel) or at 300 mM NaCl (right panel). The complexes were run on a 4-12% PAGE gradient containing SDS, then silver stained. The positions of emH2A1.1 and PARP-1 are indicated. M, protein molecular mass marker. The right panel presents the quantification of PARP-1 (relative to histone H1) within the WT and mutated emH2A1.1 complexes, isolated in 150 mM and 300 mM NaCl, respectively. Note the drastic decrease of the amount of PARP-1 within the mutated mH2A1.1 complex isolated at 300 mM NaCl.
Figure 19:
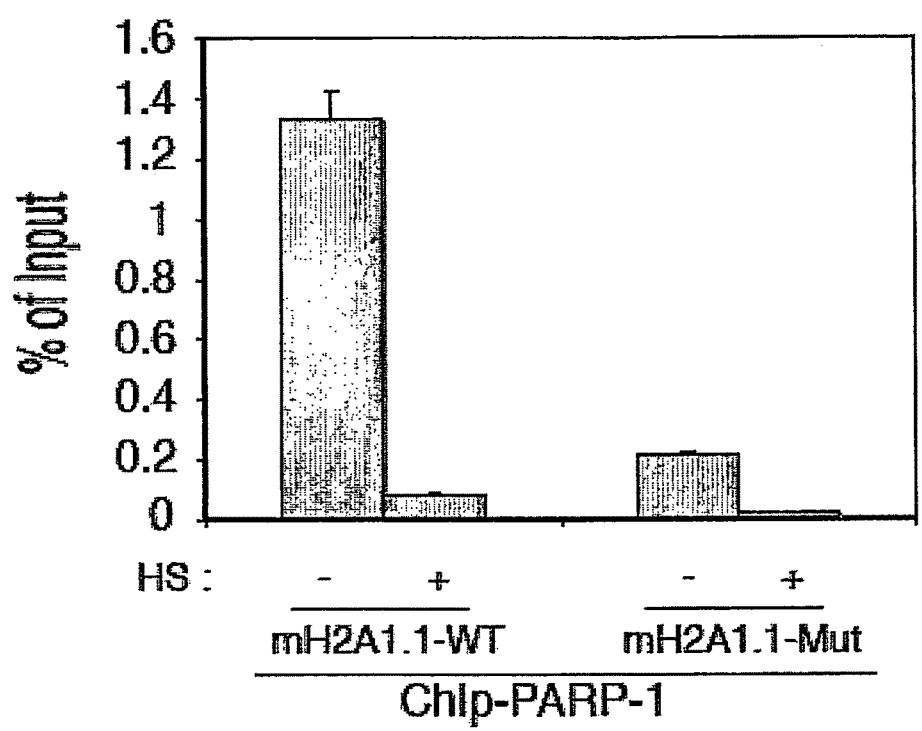
FIG. 19 shows the amount of PARP-1 associated in vivo with the Hsp70.1 promoter in non-heat-shocked (HS: −) or heat-shocked (for 30 min at 42° C.; HS: +) stable cell lines expressing wild type (WT) or mutated e-mH2A1.1 (mH2A1.1-Mut). The cell lines were treated with formaldehyde to crosslink the proteins to DNA, and ChIP was carried out using anti-PARP-1 antibody. Amounts of the real time PCR amplified Hsp70.1 promoter DNA fragments are presented as a percent of input DNA.

The results show that remarkably, the amount of PARP-1 associated with the WT and Mut complexes isolated at 150 mM NaCl differed only slightly (see the quantification at FIG. 18, right panel). However, the picture was completely different for the complexes isolated at 300 mM NaCl (FIG. 18, middle panel and quantification). In this case the amount of PARP-1 that remained associated with the mutated e-mH2A1.1 nucleosome complex did not exceed 8-10% of that associated with the WT emH2A1.1 nucleosome complex (FIG. 18, quantification). Therefore, 300 mM NaCl was able to strongly perturb the binding of PARP-1 to the mutated e-mH2A1.1 within the nucleosome complex, arguing for weaker interaction between PARP-1 and the mutated emH2A1.1. This suggests that, in vivo at the Hsp70.1 promoter, the amount of PARP-1 associated with mutated e-mH2A1.1 would be smaller compared to that associated with the WT e-mH2A1.1. We found this indeed to be the case (FIG. 19). Briefly, we have performed ChIP experiments with anti-PARP-1 by using chromatin isolated from HeLa cell lines stably expressing either WT or mutated e-mH2A1.1, and Q-PCR to quantify the amount of PARP-1-associated Hsp70.1 promoter. The quantification showed that no more than 15% of Hsp70.1 promoter was associated with PARP-1 in the cells expressing the mutated e-mH2A1.1 as compared to that found in the cells expressing the WT protein. Taken together, all the above data demonstrate, both in vitro and in vivo, that the folding of mH2A1.1 is crucial for the binding of PARP-1 to chromatin.

Figure 20:
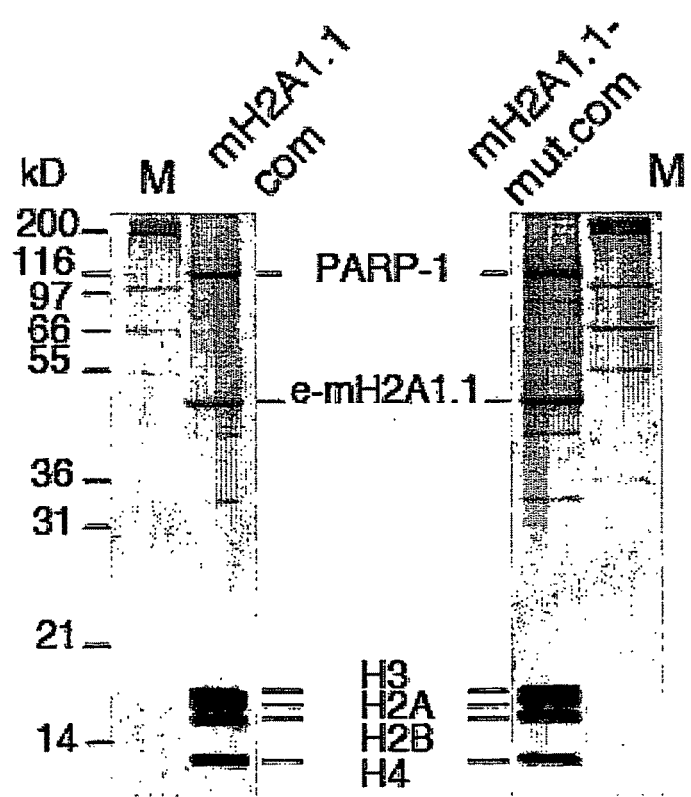
FIG. 20 shows the silver staining of the purified wild type macroH2A1.1 (e-mH2A1.1) and the mutant (e-mH2A1.1-mut) nucleosomes used for measurement of PARP-1 enzymatic activity. The complexes were isolated using 100 mM NaCl. The bands corresponding to PARP-1, e-mH2A1.1 and the conventional core histones are indicated. M, protein molecular mass marker.

We have next measured the auto-ADP ribosylation activity of the PARP-1 associated with the mutant and wild type e-mH2A1.1 nucleosome complexes. The two complexes were isolated under the same conditions by double immunoaffinity purification in a buffered solution containing 100 mM NaCl (FIG. 20). Under these conditions, the relative amount of PARP-1 associated with the mH2A1.1-mut complex was the same as that associated with the wild type mH2A1.1 complex (FIG. 20).

To measure the auto-ADP ribosylation activity of PARP-1, wild type and mutant complexes containing the same amount of associated PARP-1 were incubated in presence of mono-nucleosomes and $^{32}$P-α-NAD$^+$. The poly(ADP-ribosylation was performed in vitro in a 20 μl reaction mixture containing 20 mM Tris-HCl, pH 7.8, 50 mM NaCl, 3 mM MgCl2, 0.5 mM DTT, 10 μM {$^{32}$P}NAD (10 μCi/nmol) (AMERSHAM), 100 ng mononucleosomes prepared as described in DUBAND-GOULET et al. (Methods, vol. 33(1), p: 12-7, 2004) and 100 ng recombinant PARP-1 (ALEXIS), native macroH2A1.1 associated PARP-1 or native macro-H2A1.1 mutant associated PARP-1. The ADP ribosylation reactions were incubated at 37° C. for 1 to 30 min and stopped with 1% SDS and directly loaded on a 12% SDS-PAGE gel.

The results show that the incubation of the wild type macro-H2A1.1 complex with mononucleosomes in the presence of $^{32}$P-NAD+ results in a very poor labeling of PARP-1 (see FIG. 12), and we could hardly detect labeling after 30 min incubation. The control containing the same amount of recombinant PARP-1 (50 ng) and mononucleosomes showed a very strong labeling of PARP-1 after only 1 min incubation, suggesting that macro-H2A1.1 interferes with PARP-1 auto-ADP-ribosylation activity. The same experiment performed with macroH2A1.1 mutant complex results in a detectable labeling of PARP-1 after just 1 min incubation with $^{32}$P-NAD+ (see FIG. 12), and this labeling increases linearly until all the 32P-NAD+ is converted to ADP-ribose polymer.

Figure 21:
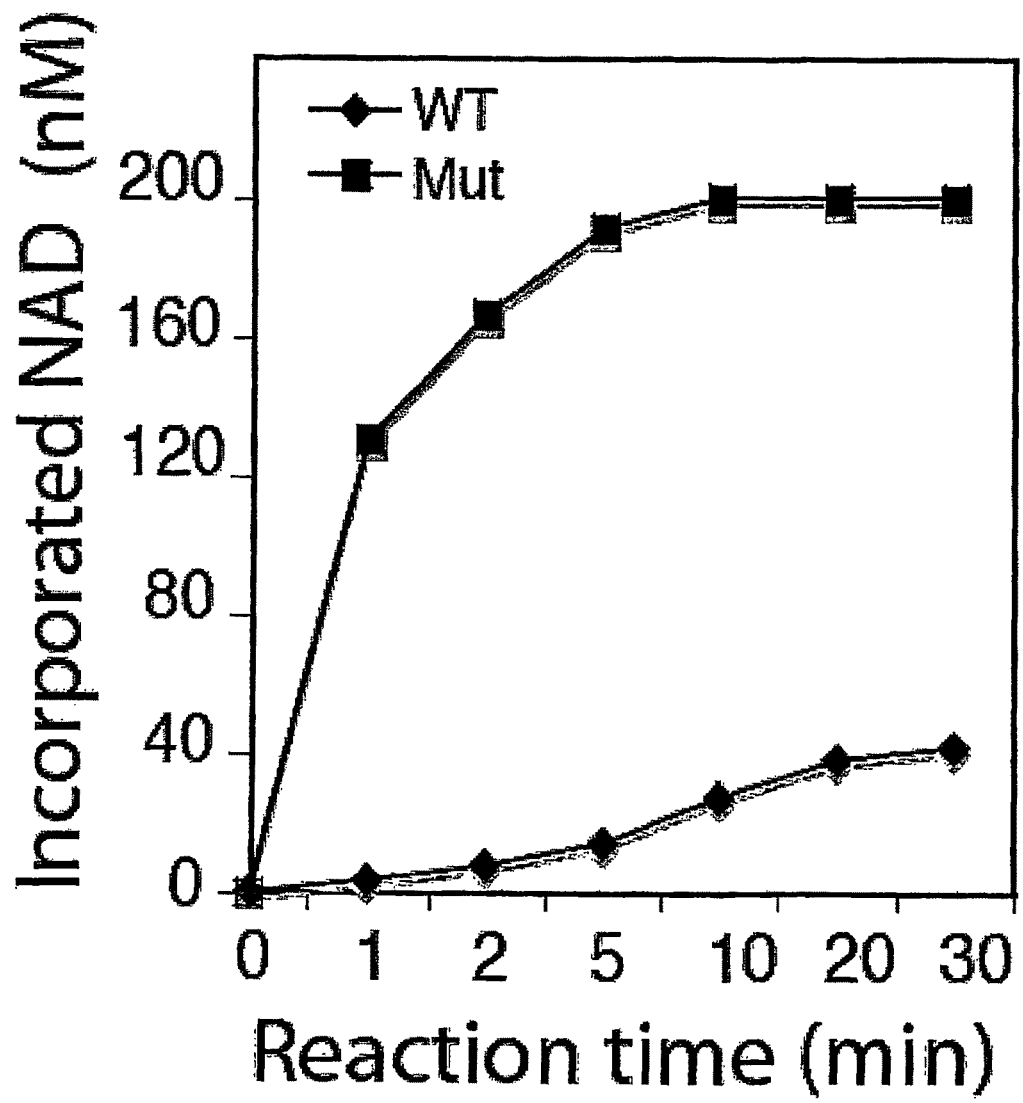
FIG. 21 shows the quantification of the data shown in FIG. 12.

In addition, the extent of PARP-1 labeling during the first minute was at least 37 times much higher than that of the PARP-1 associated with the wild type e-mH2A1.1 nucleosomes (FIG. 21, quantification).

Figure 12:
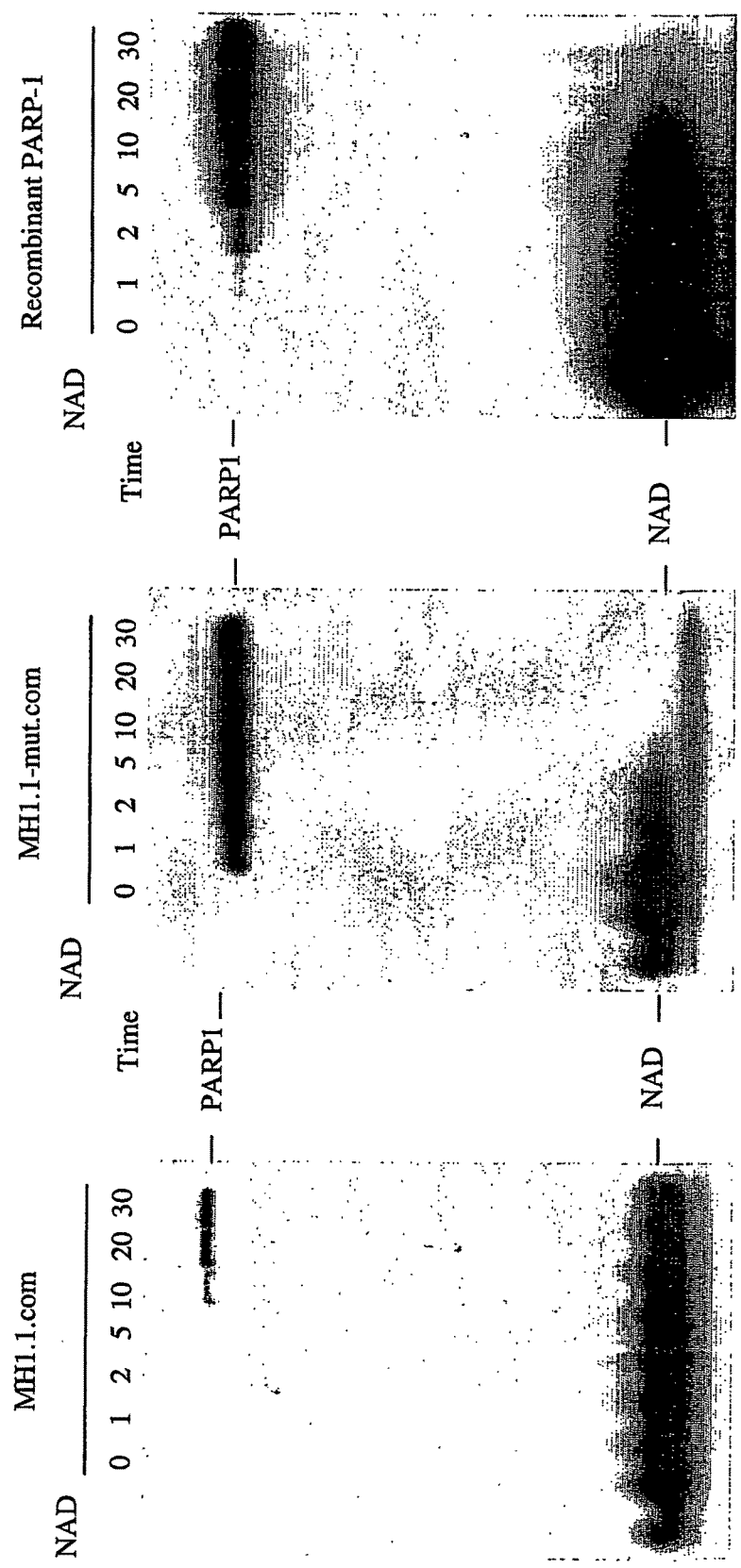
FIG. 12 shows the kinetic analysis of PARP-1 auto-ADP-ribosylation activity of recombinant PARP-1, purified macroH2A1.1 complex (MH1.1), or purified macroH2A1.1 mutant complex (MH1.1-mut.com) in the presence of $^{32}$P-NAD+.

These results strongly suggest that the interaction of mH2A1.1 with PARP-1 interferes with the PARP-1 auto-ADP-ribosylation activity. Indeed, the folding of the mutated mH2A1.1 being perturbed (FIGS. 17 and 18), this would result in a perturbation of the specific interaction between the mutated mH2A1.1 and PARP-1 (FIG. 18), which in turn would allow PARP-1 to adopt a conformation close to that of the enzyme free in solution, with higher enzymatic activity. Our data on the auto ADP-ribosylation of recombinant PARP-1 are in agreement with this, since both the kinetics and the degree of auto-ADP ribosylation of recombinant PARP-1 were similar to these of the PARP-1 associated with the mutant emH2A1.1 (FIG. 12, compare the middle and the right panel). Finally, the NAD concentration used here are close to the physiological concentrations and do not allow the formation of a highly branched PARP-1 (data not shown).

Figure 22:
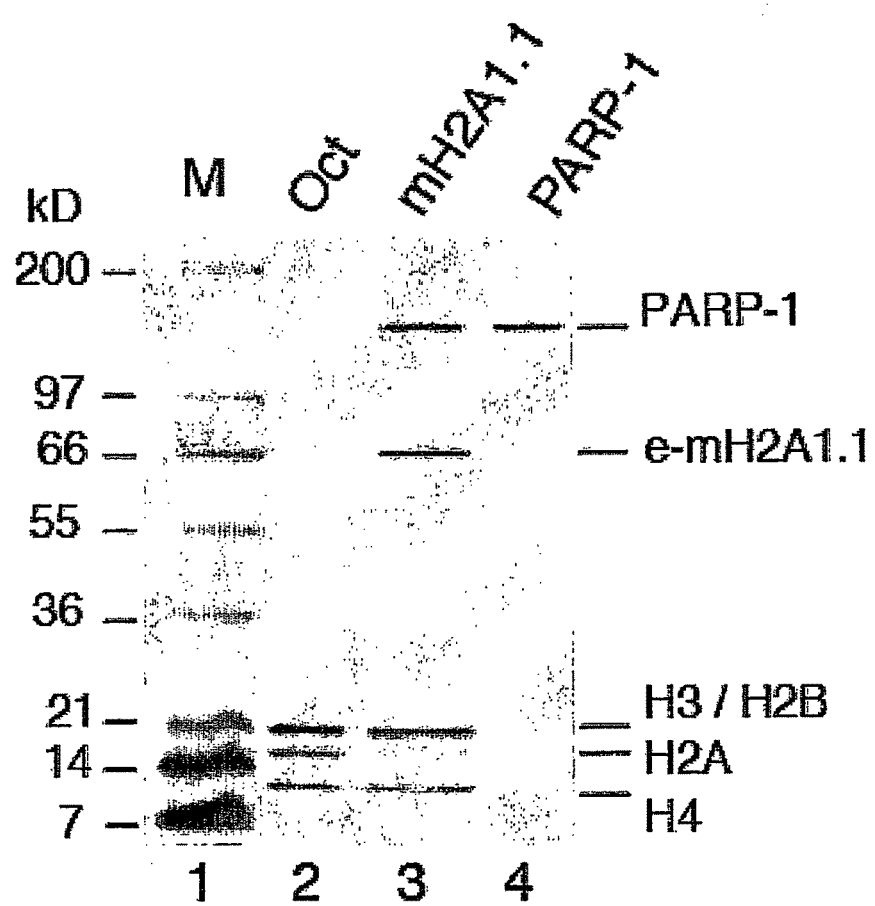
FIG. 22 shows 12% SDS-PAGE of the purified e-mH2A1.1 octamers and associated PARP-1. e-mH2A1.1 nucleosome complexes were loaded on a hydroxyl apatite column and after washing with 0.65M NaCl the remaining proteins were eluted with 2M buffered solution of NaCl. To purify PARP-1 from the histone octamers, the 2M NaCl eluate was supplemented with 1 M urea and passed through an Agarose-nickel column. Lane 3, the protein composition of the 2M NaCl eluate. Lane 4, the purified PARP-1. Lanes 1 and 2, molecular mass marker and conventional histone octamer as a control.

Since the e-mH2A1.1 mononucleosome complex contains, in addition to PARP-1, a number of other proteins it is difficult to completely exclude the possibility that some of these proteins might, as e-mH2A1.1, interact with PARP-1 and interfere also with its enzymatic activity. To rule out this we sought to purify the emH2A1.1 octamers and the associated PARP-1, to reconstitute e-mH2A1.1 nucleosome-PARP-1 complex from highly purified components and to measure the enzymatic activity of the associated with e-mH2A1.1 nucleosome PARP-1. To this end, we have generated a new HeLa cell line stably expressing a triple tagged version of mH2A1.1 (FLAG-HA-HIS). This has allowed the purification of the e-mH2A1.1 histone octamer and PARP-1 from the emH2A1.1 nucleosome complex. Briefly, the FLAG-HA purified mononucleosomes were adsorbed on a hydroxyl apatite column and washed with 0.65 M NaCl. The washing of the column with 0.65 M NaCl released all of the associated proteins, with the exception of PARP-1, (FIG. 22, lane 3, and data not shown), evidencing for a very strong binding of PARP-1 to e-mH2A1.1 nucleosomes (to note is that the remaining on the column e-mH2A1.1 and PARP-1 are in roughly stoichiometric amount, suggesting that one molecule of nucleosomal emH2A1.1 might be complexed with one molecule of PARP-1).

Figure 23:
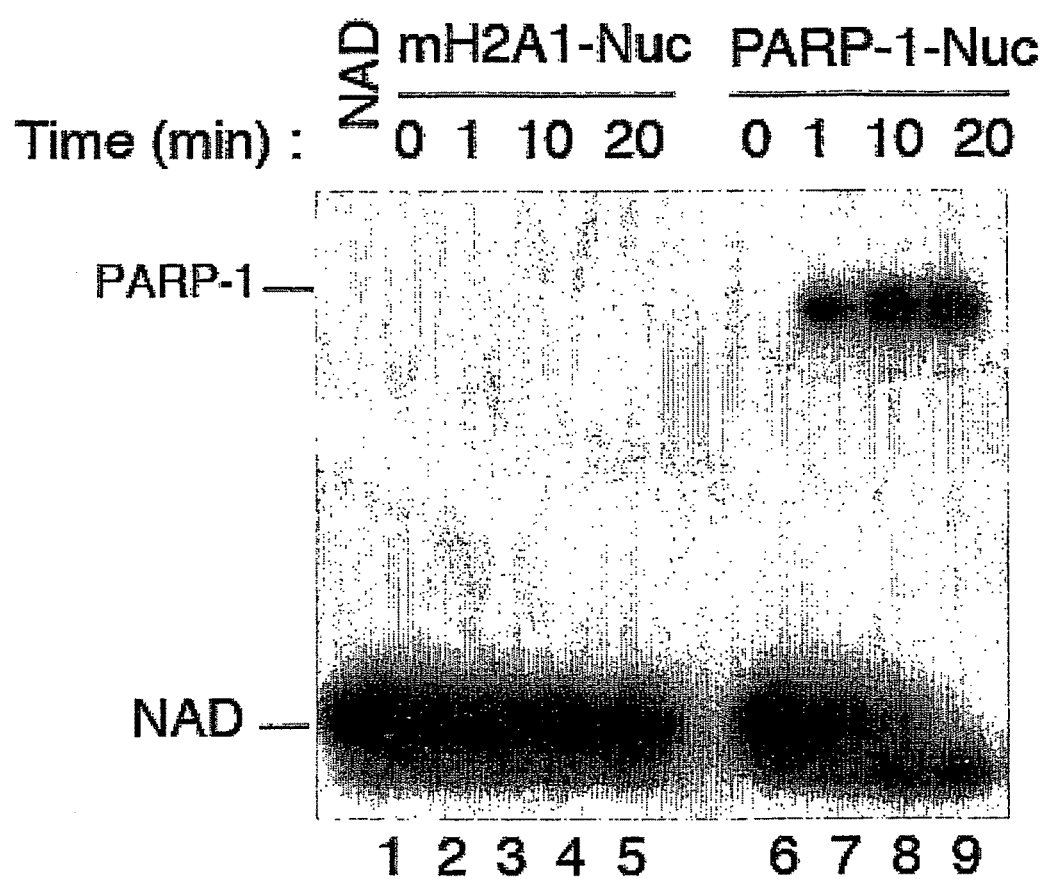
FIG. 23 shows the kinetic analysis of PARP-1 activity associated with in vitro reconstituted nucleosomes containing either purified e-mH2A1.1 core histones (lanes, 6-9) or conventional core histones (lanes, 2-5). The samples were incubated with $^{32}$P-NAD$^+$ and run on 12% PAGE containing SDS. Lane 1, contains $^{32}$P-NAD$^+$ only.

The e-mH2A1.1 octamer and PARP-1 were released from the column with a buffered solution containing 2M NaCl (FIG. 22, lane 3) and were used for reconstitution of emH2A1.1-PARP-1 nucleosome complex. The auto-ADP ribosylation activity of the PARP-1 associated with the reconstituted e-mH2A1.1 nucleosomes was then tested (FIG. 23). A solution containing conventional nucleosomes and native PARP-1 (purified from the 2M NaCl eluate of the hydroxyl apatite column immobilized e-mH2A1.1 nucleosome complex (FIG. 22, lane 4), was used as a positive control (FIG. 23). The reaction was arrested at the indicated times and the samples loaded on a 12% SDS-PAGE gel. After completion of electrophoresis, the auto-ADP-ribosylated PARP-1 was visualized by autoradiography (FIG. 23). Incubation of the in vitro reconstituted emH2A1.1 nucleosomes with PARP-1 in presence of $^{32}$P-α-NAD$^+$ resulted in a complete inactivation of its enzymatic activity (FIG. 23, lanes 2-5), while the same PARP-1, when incubated with conventional mononucleosomes, showed a strong ADP-ribosylation activity, which increased with time and reached completion within 10-20 minutes (FIG. 23, lanes 6-9). In addition, incubation of the in vitro reconstituted mH2A1.1 nucleosomes containing PARP-1 in the presence of a 100 fold excess of conventional nucleosomes failed to reactivate PARP-1 (data not shown), further confirming that the specific interaction between PARP-1 and mH2A1.1 determines the "inactivation" of the enzyme.

10) Identification of the PARP-1 Binding Site in the C-Terminal Non Histone Region of MacroH2A1.1

To identify the domain of macroH2A1.1 specifically interacting with PARP-1, we perform GST-pull down experiments using recombinant macroH2A1.1 non-histone region with different deletions as bait. The experiments are realized as described previously. As control experiments, we use recombinant macroH2A1.1 non-histone region with G224E, which abolish binding of ADP ribose (KUSTATSCHER et al., 2005, abovementioned), and recombinant macro domain of YBR022w (from S. Cerivisiae; NP_009578) as baits.

In order to identify corresponding binding region in macroH2A1.2 and in macroH2A2, we also perform GST-pull down experiments using recombinant macroH2A1.2 or macroH2A2 non-histone region with different deletions as bait.

11) Recombinant Inhibitors of PARP-1 Activity

In order to identify new inhibitor of PARP-1 activity, we elaborate different constructions encoding for GST fusion proteins containing the macroH2A1.1 binding site to PARP-1 fused to the macro domain of macroH2A1.2, macroH2A2, or YBR022w (from S. Cerivisiae; NP_009578).

The recombinant proteins are produced as described previously, and purified according to standard protocols.

We perform poly(ADP-ribosylation assay in the presence of recombinant PARP-1 (ALEXIS) with or without the different GST fusion proteins containing the macroH2A1.1 binding site to PARP-1.

I claim:

1. An isolated inhibitor of the nucleic enzyme poly(adenosine 5'-diphospho-ribose) polymerase (PARP) having phosphoesterase activity, comprising: an amino acid sequence consisting of macroH2A1.1 (amino acids 121 to 369 of SEQ ID NO: 1), macroH2A1.2 (amino acids 120 to 371 of SEQ ID NO: 2), or macroH2A2 (amino acids 121 to 372 of SEQ ID NO: 3), wherein the amino acid sequence is fused to a heterologous sequence selected from the group consisting of a nuclear localization sequence, a His tag, a GST protein, a FLAG tag, an HA tag, and combinations thereof.

2. The isolated inhibitor of PARP of claim 1, wherein the amino acid sequence is a C-terminal non-histone domain of macroH2A1.1.

3. The isolated inhibitor of PARP of claim 1, wherein the macroH2A1.1, macroH2A1.2, or macroH2A2 do not comprise a macroH2A histone fold domain that is homologous with histone H2A.

4. The isolated inhibitor of PARP of claim 1, wherein the macroH2A1.1, macroH2A1.2, or macroH2A2 comprise the macro domain of a macroH2A histone.

5. The isolated inhibitor of PARP of claim 4, wherein the macro domain of a macroH2A histone is selected from the group consisting of residues 184 to 369 or 202 to 369 of macroH2A1.1 (SEQ ID NO: 1), residues 183 to 371 or 201 to 371 of macroH2A1.2 (SEQ ID NO: 2), and residues 184 to 372 or 202 to 372 of macroH2A2 (SEQ ID NO: 3).

6. A composition comprising:
(i) the isolated inhibitor of PARP of claim 1, and
(ii) a pharmaceutically acceptable vehicle.

7. An isolated inhibitor of the nucleic enzyme poly(adenosine 5'-diphospho-ribose) polymerase (PARP) in a composition for treating neurological disorders, cardiovascular disorders, immune senescence diseases, degenerative diseases, or inflammatory disorders associated with PARP activation, comprising:
a C-terminal non-histone domain of a macroH2A histone having an amino acid sequence consisting of macroH2A1.1 (amino acids 121 to 369 of SEQ ID NO: 1), macroH2A1.2 (amino acids 120 to 371 of SEQ ID NO: 2), or macroH2A2 (amino acids 121 to 372 of SEQ ID NO: 3) histone, wherein the amino acid sequence is fused to a nuclear localization sequence, a His tag, a GST protein, a FLAG tag, an HA tag, or a combination thereof.

8. The isolated inhibitor of PARP of claim 7, wherein the C-terminal non-histone domain of macroH2A histone is macroH2A1.1.

9. The isolated inhibitor of PARP of claim 7 wherein the macroH2A1.1, macroH2A1.2, or macroH2A2 do not comprise a macroH2A histone fold domain that is homologous with histone H2A.

10. The isolated inhibitor of PARP of claim 7, wherein the amino acid sequence consists of residues 184 to 369 or 202 to 369 of macroH2A1.1 (SEQ ID NO: 1), residues 183 to 371 or 201 to 371 of macroH2A1.2 (SEQ ID NO: 2), or residues 184 to 372 or 202 to 372 of macroH2A2 (SEQ ID NO: 3).

11. The isolated inhibitor of PARP of claim 7, comprising a pharmaceutically acceptable vehicle.

12. An isolated inhibitor of the nucleic enzyme poly(adenosine 5'-diphospho-ribose) polymerase (PARP) having phosphoesterase activity, comprising:
a C-terminal non-histone domain of a macroH2A histone fused to at least one heterologous sequence, wherein the C-terminal non-histone domain of the macroH2A histone has an amino acid sequence consisting of macroH2A1.1 (amino acids 121 to 369 of SEQ ID NO:1) and the heterologous sequence is selected from the group consisting of a nuclear localization sequence, a His tag, a GST protein, a FLAG tag, an HA tag, and combinations thereof.

13. An isolated inhibitor of the nucleic enzyme poly(adenosine 5'-diphospho-ribose) polymerase (PARP) having phosphoesterase activity, comprising:
an amino acid sequence consisting of residues 184 to 369 or 202 to 369 of human macroH2A1.1 (SEQ ID NO: 1), residues 183 to 371 or 201 to 371 of human macroH2A1.2 (SEQ ID NO: 2), or residues 184 to 372 or 202 to 372 of human macroH2A2 (SEQ ID NO: 3), wherein the amino acid sequence is fused to a heterologous sequence selected from the group consisting of a nuclear localization sequence, a His tag, a GST protein, a FLAG tag, an HA tag, and combinations thereof.

* * * * *